(12) United States Patent
Segade Rodríguez et al.

(10) Patent No.: US 8,981,105 B2
(45) Date of Patent: Mar. 17, 2015

(54) PROCESS OF PREPARING A THROMBIN SPECIFIC INHIBITOR

(75) Inventors: Antoni Segade Rodríguez, Barcelona (ES); Mireia Pastó Aguilá, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 0 days.

(21) Appl. No.: 13/809,320

(22) PCT Filed: Jul. 8, 2011

(86) PCT No.: PCT/EP2011/061678
§ 371 (c)(1),
(2), (4) Date: Jan. 9, 2013

(87) PCT Pub. No.: WO2012/004396
PCT Pub. Date: Jan. 12, 2012

(65) Prior Publication Data
US 2013/0116440 A1    May 9, 2013

(30) Foreign Application Priority Data

Jul. 9, 2010 (ES) .................................. 201031049

(51) Int. Cl.
*C07D 401/00* (2006.01)
*A61K 31/44* (2006.01)
*C07D 401/12* (2006.01)
*C07D 401/04* (2006.01)

(52) U.S. Cl.
CPC ............ *C07D 401/12* (2013.01); *C07D 401/04* (2013.01)
USPC ....................................... 546/273.4; 514/341

(58) Field of Classification Search
None
See application file for complete search history.

(56) References Cited

U.S. PATENT DOCUMENTS

| 7,202,368 B2 | 4/2007 | Zerban et al. |
| 7,459,566 B2 | 12/2008 | Zerban et al. |
| 2006/0247278 A1 | 11/2006 | Sieger et al. |

FOREIGN PATENT DOCUMENTS

| CA | 2277949 C | 10/2006 |
| CA | 2476054 C | 11/2011 |
| WO | WO98/37075 A1 | 8/1998 |
| WO | WO03/074056 A1 | 9/2003 |
| WO | WO 2006/000353 A1 | 1/2006 |
| WO | WO 2006/114415 A2 | 11/2006 |
| WO | WO 2008/043759 A1 | 4/2008 |
| WO | WO 2008/095928 A1 | 8/2008 |
| WO | WO 2009/111997 A1 | 9/2009 |
| WO | WO 2009/153214 A1 | 12/2009 |
| WO | WO 2010/045900 A1 | 4/2010 |

OTHER PUBLICATIONS

Hauel N. H. et al, "Structure-Based Design of Novel Potent Non-Peptide Thrombin Inhibitors", Journal of Medicinal Chemistry, American Chemical Society, Jan. 2002, vol. 45, No. 9, pp. 1757-1766, Published on Web Mar. 26, 2002, XP-001098844, Washington DC, US.
L.A. Sorbera et al., "Dabigatran/Dabigatran etexilate", Drugs of the Future, Prous Science, vol. 30, No. 9, Jan. 2005, pp. 877-885, Barcelona, Spain.
International Search Report and Written Opinion for PCT International Application No. PCT/EP2011/061678 issued by the European Patent Office dated May 11, 2012, Rijswijk, Netherlands.
International Search Report for WO2012/004396A3; PCT International Application No. PCT/EP2011/061678 published by WIPO dated Jan. 12, 2012, Geneva, Switzerland.
International Search Report and Written Opinion for PCT International Application No. PCT/EP2011/061680 issued by the European Patent Office dated Sep. 5, 2011, Rijswijk, Netherlands.
International Preliminary Report on Patentability for PCT International Application No. PCT/EP2011/061680 published by WIPO on Jan. 15, 2013, Geneva Switzerland.
Written Opinion for PCT International Application No. PCT/EP2011/061680 published by WIPO on Jan. 9, 2013, Geneva Switzerland.

*Primary Examiner* — Heidi Reese
(74) *Attorney, Agent, or Firm* — Peter B. Scull; Hamilton, DeSanctis & Cha, LLP

(57) ABSTRACT

A process of preparation of a compound of formula (I), or a pharmaceutically acceptable salt thereof, wherein $R^1$ and $R^2$ represent H; or either $R^1$ represents ethyl and $R^2$ represents n-hexyloxycarbonyl that applies to industrial scale, novel intermediates useful for the preparation thereof, and processes of preparing said intermediates.

(I)

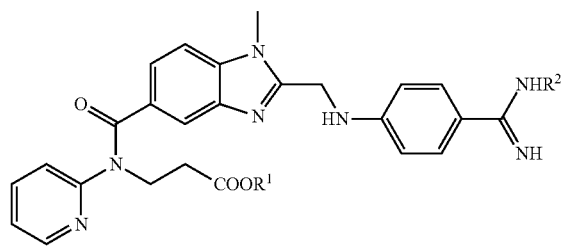

20 Claims, 11 Drawing Sheets

PROCESS OF PREPARING A THROMBIN SPECIFIC INHIBITOR

The present invention is related to a process of preparing dabigatran, dabigatran etexilate, and pharmaceutically acceptable salts thereof. It is also related to novel intermediates useful for the preparation thereof and processes of preparing said intermediates.

STATE OF THE ART

Dabigatran is the generic name of compound N-[([(amidinophenyl)-amino]methyl)-1-methyl-1H-benzimidazole-5-carbonyl]-N-(2-pyridyl)-3-aminopropionic acid, the chemical structure of which is the following:

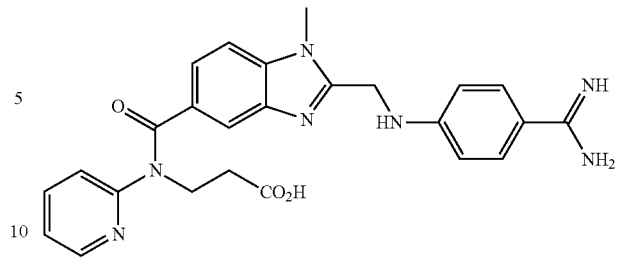

Dabigatran is a thrombin specific inhibitor that is given orally in the form of prodrug dabigatran etexilate. The latest is rapidly absorbed after oral administration and converts to dabigatran, the pharmacologically active molecule, through hydrolysis catalyzed by plasma and liver esterases. The chemical name for dabigatran etexilate is ethyl N-[([([(N'-hexyloxycarbonyl)amidino]phenyl)amino]methyl)-1-methyl-1H-benzimidazole-5-carbonyl]-N-(2-pyridyl)-3-aminopropionate, and its chemical structure, the following:

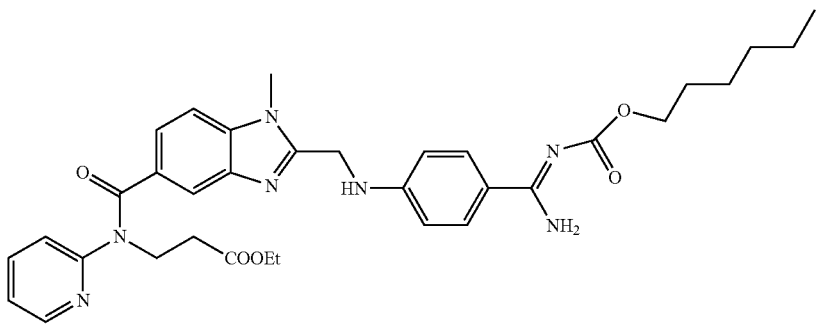 [SMILES: CCCCCCOC(=O)/N=C(\N)c1ccc(NCc2nc3cc(C(=O)N(CCC(=O)OCC)c4ccccn4)ccc3n2C)cc1]

Dabigatran and dabigatran etexilate were first described in patent application WO 98/37075. Several dabigatran etexilate salts, including the mesylate, have been described in documents WO 03/74056, WO 2006/114415 and WO 2008/43759.

The process of obtaining dabigatran and dabigatran etexilate described in patent application WO 98/37075 is based on the following synthesis scheme:

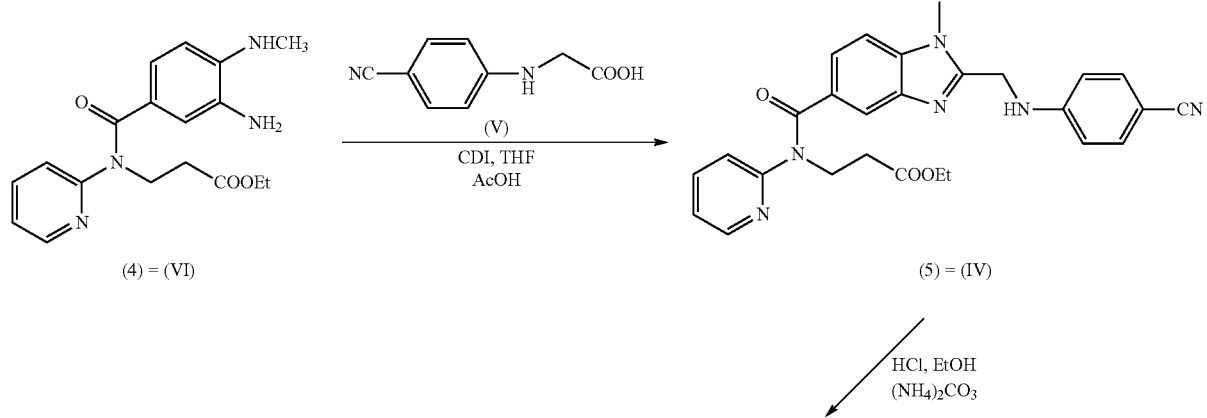

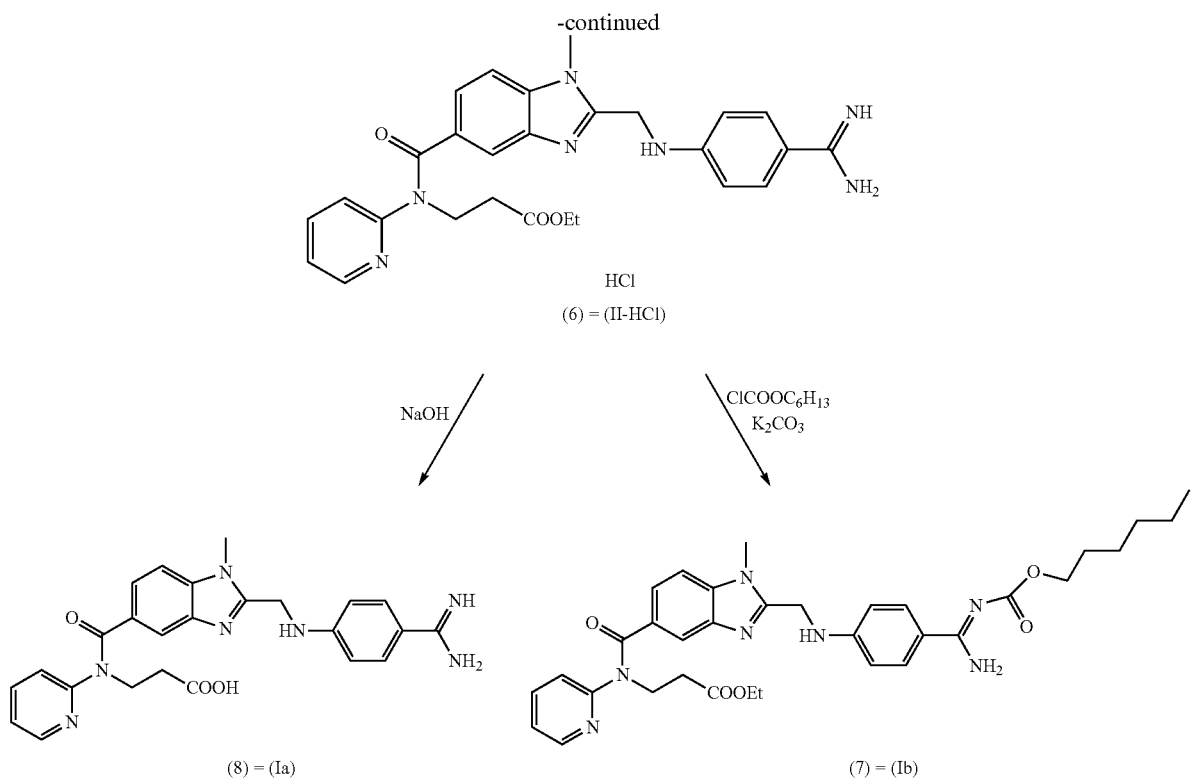

(6) = (II-HCl)

(8) = (Ia)    (7) = (Ib)

Document WO 2008/095928 describes the hydrobromide of compound (IV), and document WO 2009/111997, the oxalate of compound (IV).

Some steps in the synthesis pathway indicated above, in particular the steps of preparing compounds (IV) and (II-HCl), require the purification of the obtained compounds by chromatography, thereby these steps are not suitable to be carried out at an industrial level.

In document WO 98/37075, the compound of formula (II) is isolated in the form of a hydrochloride. The conversion of the compound of formula (IV) into the compound of formula (II), and subsequent isolation in the form of a salt other than the hydrochloride has also been described in other documents. For instance, in document WO 2008/095928 the compound of formula (II) is isolated in the form of a p-toluenesulfonate, and in document WO 2010/045900 is isolated in the form of a monohydrochloride ethanol solvate or in the form of a dihydrochloride.

The conversion of the compound of formula (IV) into the compound of formula (II) described in these patent applications requires the use of a large amount of ammonia or ammonium carbonate equivalents to form the compound of formula (II), and thus neutralize the large amount of HCl in the solution.

For example, in document WO 2008/095928 up to 11 equivalents of ammonia are added; and in documents WO 98/37075 and WO 2010/045900, up to 10 and 16 equivalents of ammonium carbonate, respectively, in relation to the starting product.

As a consequence, the process generates a large amount of residual salts to be removed in the form of $NH_4Cl$, which considerably hinders the industrial scaling up, and in some cases additionally requires tedious purifications as chromatography.

Therefore, there is a need of having alternative processes for the preparation of dabigatran and dabigatran etexilate, in particular if they are easy to industrialize.

DESCRIPTION OF THE INVENTION

The inventors have achieved to develop a process of preparing dabigatran or dabigatran etexilate that passes through the isolation of the intermediate imidate (III-HCl) that is formed in the conversion of the cyano intermediate (IV) into the amidino intermediate (II), in particular in the form of a hydrochloride.

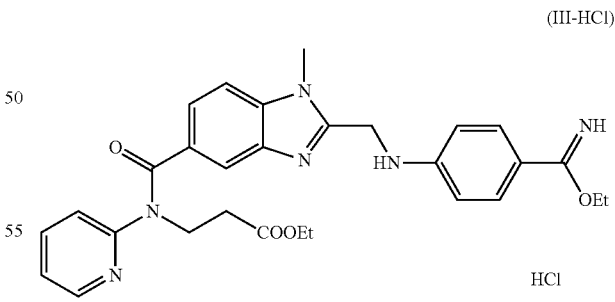

(III-HCl)

This compound of formula (III) may have more than one molecule of HCl.

The inventors have found that by isolating said imidate the problems mentioned above are solved. Specifically, the use of the isolated product as a solid allows considerably reducing the amount of ammonia or ammonium salt (between 3-5 equivalents in relation to the starting compound in the subsequent step). Moreover it allows the obtention of the compound of formula (II-HCl) by a process that generates a much smaller amount of salts than the processes known in the state of the art, and runs with high chemical purity and without the need of chromatographic purification.

In particular, the use of 11 equivalents of ammonia, such as is described in document WO 2008/095928, generates about 0.5 Kg of salts for each mol of amidino compound formed, while the use of 3 equivalents of ammonia according to the process of the invention generates about 0.1 Kg of salts for each mol of amidino compound formed.

Likewise, the reduction of the amount of salts generated (insoluble in the reaction medium) allows the use of a smaller volume of solvent in the reaction, with the savings that entails, and facilitates the crystallization of the product free of salts, avoiding a chromatographic purification of difficult industrial application.

This fact has the additional advantage that avoids contamination of the amidino compound with $NH_4Cl$, which is detrimental for the next step of the synthesis, i.e. the preparation of the etexilate, as these residues consume part of the n-hexyl haloformate necessary for the conversion to dabigatran etexilate.

Therefore, the process of preparing dabigatran that comprises the transformation above-mentioned results more suitable from the industrial point of view than the processes known in the state of the art.

The rest of the steps described in the present invention represent also a significant improvement in relation to the processes already described. Additionally, when the different steps in the present invention are carried out together the resulting process is a particularly effective industrializable process.

On the other side, the inventors have also found novel solid forms of intermediates other than the compound of formula (III-HCl) that show high purities and contribute to the optimization of the process of preparing dabigatran. The isolation of these intermediates in solid form results advantageous in that contributes to obtain a final product with a high purity without the need of chromatographic purification.

A first aspect of the invention relates to a process of preparing a compound of formula (I), or a pharmaceutically acceptable salt thereof, or a pharmaceutically acceptable solvate thereof, including a hydrate,

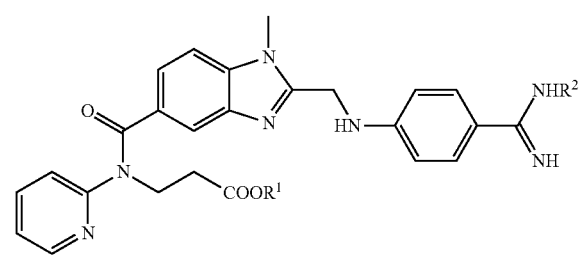

(I)

wherein $R^1$ and $R^2$ represent H; or either $R^1$ represents ethyl and $R^2$ represents n-hexyloxycarbonyl, comprising a) providing the compound of formula (III-HCl) as a solid;

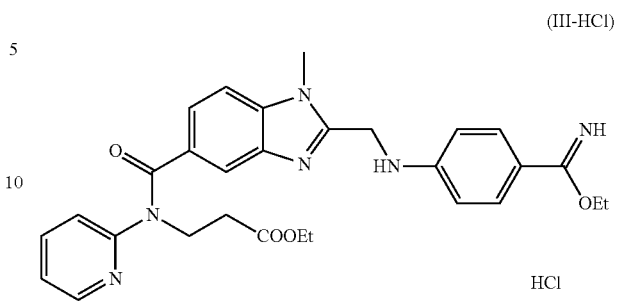

(III-HCl)

b) reacting the compound of formula (III-HCl) with an amount comprised between 3-5 mol of ammonia or an ammonium salt for each mol of the compound of formula (III-HCl) to obtain the compound of formula (II-HCl);

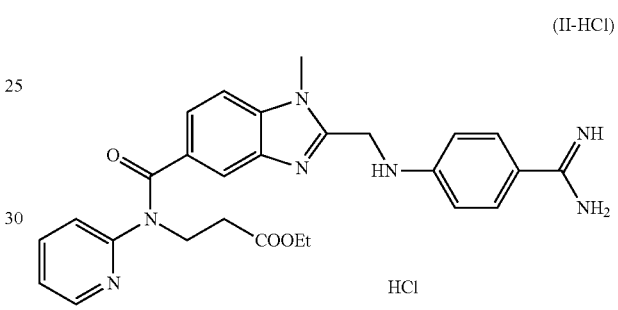

(II-HCl)

and isolating the product obtained as a solid;
c) converting the compound of formula (II-HCl) obtained into a compound of formula (I); and
d) optionally converting the compound of formula (I) in a pharmaceutically acceptable salt thereof by treatment with an acid, or either converting a pharmaceutically acceptable salt of the compound of formula (I) into a compound of formula (I) by treatment with a base, or either converting a salt of the compound of formula (I) into another salt of the compound of formula (I) by ion exchange.

The conversion of the compound of formula (III-HCl) into the compound of formula (II-HCl) takes place by reaction with ammonia or an ammonium salt, such as ammonium carbonate or ammonium acetate. In a preferred embodiment, the ammonium salt is $(NH_4)_2CO_3$. Typically, the $NH_3$ source used may be solid $(NH_4)_2CO_3$, $NH_3$ solutions in water or organic solvents. Generally, these organic solvents may be $(C_1-C_6)$alcohols, such as methanol or ethanol; or $(C_3-C_6)$ethers such as tetrahydrofuran or dioxane. The use of $NH_3$ solutions in organic solvents is preferred, because the hydrolysis of the imidate salt is then minimized.

Generally, between 1-8 mol of ammonia or ammonium salt are used for each mol of the compound of formula (III-HCl), more preferably between 3-5 mol. In the most preferred embodiment, 3 mol of ammonia are used for each mol of the compound of formula (III-HCl).

This reaction is carried out within a solvent, as e.g. in a $(C_1-C_6)$alcohol such as methanol, ethanol or isopropanol; a $(C_3-C_8)$ketone, such as acetone, methylethylketone or methylisobutylketone; a $(C_1-C_6)$alkyl $(C_1-C_6)$ester, such as ethyl acetate; a $(C_3-C_6)$amide, such as dimethylformamide, dimethylacetamide or N-methylpyrrolidone; or a $(C_3-C_6)$ether such as tetrahydrofuran or dioxane. Preferably, the reaction is carried out in a ($C_1$-$C_6$)alcohol, more preferably in ethanol.

The reaction can be performed within a temperature range between 0-100° C., being room temperature the preferred temperature for the reaction.

Once the reaction is completed (typically 24-48 h), as it was initiated with the compound of formula (III-HCl) in solid form, it is possible to minimize the volume of the solution containing the compound of formula (II-HCl) before filtering the insoluble salts. As a consequence, the amount of solubilized $NH_4Cl$ is minimized, a fact that allows for better purification of the product. As a way of example, when the reaction is performed in ethanol, it is possible to reduce the volume of the solution to about 5 volumes in relation to the starting imidate salt.

Subsequently, the product is isolated by substituting or mixing the reaction solvent with an antisolvent that makes the compound of formula (II-HCl) insoluble. The possible antisolvents may be a ($C_3$-$C_8$)ketone, such as acetone, methylethylketone or methylisobutylketone; a ($C_1$-$C_6$)alkyl ($C_1$-$C_6$) ester, such as ethyl acetate; a ($C_3$-$C_6$)amide, such as dimethylformamide, dimethylacetamide or $\underline{N}$-methylpyrrolidone; a ($C_3$-$C_6$)ether such as tetrahydrofuran or dioxane; a ($C_6$-$C_9$)aromatic solvent such as toluene or xylene; a ($C_5$-$C_{12}$)alkane such as heptane; ($C_5$-$C_{12}$)cycloalkane such as cyclohexane or a ($C_3$-$C_6$) alcohol. The preferred antisolvent is toluene, as it allows the removal of the ethanol by azeotropic distillation, obtaining the compound of formula (II-HCl) as a solid with a purity higher than 90%, and contaminated only with small amounts of $NH_4Cl$.

Additionally, the solid obtained may be recrystallized, preferably from isopropanol, obtaining a crystalline compound of defined and characterized structure, of a higher than 99% purity and absolutely free of $NH_4Cl$. The compound of formula (II-HCl) is obtained in document WO 98/37075 after purification by chromatography. Following the process of the present invention, the inventors have achieved to isolate the compound of formula (II-HCl) in crystalline form, which is also part of the invention.

Thus, another aspect of the invention relates to the compound of formula (II-HCl), i.e., ethyl $\underline{N}$-([[[(amidino)phenyl]-amino)methyl]-1-methyl-1$\underline{H}$-benzimidazole-5-carbonyl)-$\underline{N}$-(2-pyridyl)-3-aminopropionate hydrochloride (II-HCl) in crystalline form.

Depending on the crystallization and on drying conditions, different polymorphic forms of the compound of formula (II-HCl) may be obtained.

In a preferred embodiment a crystalline form of the compound of formula (II-HCl) essentially free from other crystalline forms is provided, hereinafter called form I, that shows an X-Ray powder diffraction pattern comprising 2θ angle values at 6.8, 7.8, 9.2, 11.7, 12.3, 15.6, 18.4, 23.5 measured in an X-ray diffractometer with Cu Kα radiation (1.5418 Å). In a more preferred embodiment, the crystalline form of the compound of formula (II-HCl) shows an X-Ray powder diffraction pattern substantially according to FIG. 6.

By the term "essentially free from other crystalline forms" it is meant that the total ratio of other possible polymorphic forms is equal to or less than 10% by weight. Preferably, is equal to or less than 5% by weight, more preferably is equal to or less than 3% by weight, and even more preferably is equal to or less than 1% by weight. The way of determining the percentage may be performed by comparison with mixtures of pure polymorphs standards in the indicated ratios.

This crystalline form of the compound of formula (II-HCl) may have a variable amount of water depending on the environmental conditions.

In another preferred embodiment, a crystalline form of the compound of formula (II-HCl) is provided, hereinafter called form V, which is essentially free from other crystalline forms, and that shows an X-Ray powder diffraction pattern comprising 2θ angle values at 6.7, 9.4, 14.1, 17.6, 18.0, 19.8, 21.9, 23.6, 24.0, 27.7 measured in an X-ray diffractometer with Cu Kα radiation (1.5418 Å). In a more preferred embodiment, this crystalline form of the compound of formula (II-HCl) shows an X-Ray powder diffraction pattern substantially according to FIG. 7.

The form I of the compound of formula (II-HCl) is considered especially appropriate for obtaining dabigatran etexilate or pharmaceutically acceptable salts thereof, as it allows the isolation of this intermediate in solid form, facilitating its purification, as well as its manipulation as it is a stable form with appropriate properties for industrial-scale manipulation. The same happens with the form V of the compound of formula (II-HCl), which is highly crystalline and has mechanical properties that make it especially appropriate to be manipulated at an industrial scale, as e.g. its good filtration ability.

It is also part of the invention, the provision of other polymorphic forms of the compound of formula (II-HCl), in particular, the form II, the form III and the form IV, which are useful as intermediates for the preparation of the form I.

The form II shows an X-Ray powder diffraction pattern comprising 2θ angle values at 7.0, 9.2, 10.2, 11.9, 12.4, 16.0, and 18.4 measured in an X-ray diffractometer with Cu Kα radiation (1.5418 Å). Preferably, the crystalline form II of the compound of formula (II-HCl) shows an X-Ray powder diffraction pattern substantially according to FIG. 8.

The form III shows an X-Ray powder diffraction pattern comprising 2θ angle values at 6.2, 6.5, 10.4, 10.9, 11.2, 11.9, 12.4, 14.8, 15.3, 15.8, 15.9, 16.3, 17.5, and 18.4 measured in an X-ray diffractometer with Cu Kα radiation (1.5418 Å). Preferably, the crystalline form III of the compound of formula (II-HCl) shows an X-Ray powder diffraction pattern substantially according to FIG. 9.

The form IV shows an X-Ray powder diffraction pattern comprising 2θ angle values at 6.3, 7.4, 11.3, 15.5, 17.7, and 18.2 measured in an X-ray diffractometer with Cu Kα radiation (1.5418 Å). Preferably, the crystalline form IV of the compound of formula (II-HCl) shows an X-Ray powder diffraction pattern substantially according to FIG. 10.

Depending on the conditions of the crystallization process, it can be obtained forms II, III, IV or mixtures thereof, as well as mixtures with the form I. Upon heating, these mixtures are converted to form I.

A crystalline form of the compound of formula (II-HCl) that shows an X-Ray powder diffraction pattern comprising 2θ angle values at 6.8, 7.1, 7.8, 9.2, 11.7, 12.3, 15.6, 18.4 and 23.5 measured in an X-ray diffractometer with Cu Kα radiation (1.5418 Å) is also part of the invention. Preferably, the crystalline form shows an X-Ray powder diffraction pattern substantially according to FIG. 1. This crystalline form comprises a percentage of about 70% by weight of the crystalline form I and a percentage of about 30% by weight of the crystalline form II.

The process of preparing said crystalline form of the compound of formula (II-HCl), which is a mixture of form I and form II, is also part of the invention. This crystalline form may be obtained by crystallization of compound (II-HCl) from a solution thereof in isopropanol, at a temperature comprised between 10-80° C., and in a concentration between 3-20 volumes of isopropanol. Generally, the crystallized product is filtered at a temperature that may range between −15° C. and room temperature and is dried at room temperature under vacuum.

Carrying out this recrystallization step has the advantage that it allows the removal of the $NH_4Cl$ residues, not very convenient for the next synthesis step to proceed.

The form V essentially free from other crystalline forms may be prepared as indicated in Example 6, i.e. by subsequent recrystallizations from isopropanol and drying the solid obtained at about 65° C. under vacuum.

Depending on the temperature and atmosphere of the drying of the solid obtained, other crystalline forms may be obtained, in particular, the form II, III, or IV as illustrated in the Examples 8, 9 and 10.

The form I can also be obtained from mixtures of other crystalline forms, preferably by heating. For instance, from a mixture of forms I, II and IV, at a temperature between 60-70° C. Preferably, the temperature is about 65° C. It can also be obtained by heating a mixture of forms I and II at a temperature around 60-70° C. Preferably, the temperature is about 65° C.

Alternatively, the form I can be obtained by recrystallization in isobutanol and drying of the compound obtained at a temperature around 85° C. under vacuum. At the beginning of the drying other crystalline forms may appear. As it is illustrated in Example 7, it can be obtained form IV that is transformed in form I by heating.

The compound of formula (III-HCl) is obtained by reaction of the compound of formula (IV)

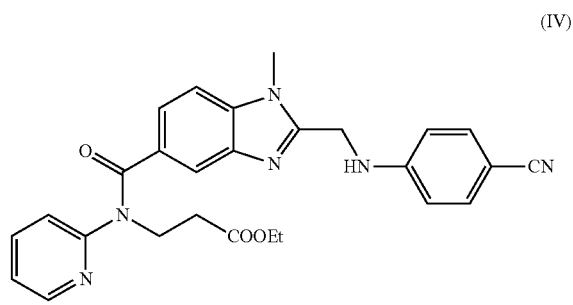 [SMILES: CCOC(=O)CCN(C(=O)c1ccc2c(c1)nc(CNc1ccc(C#N)cc1)n2C)c1ccccn1]

(IV)

or its corresponding hydrochloride (IV-HCl)

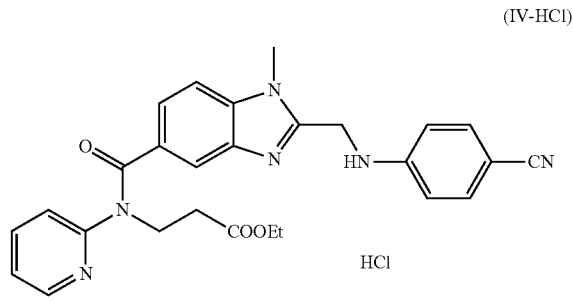 [SMILES: CCOC(=O)CCN(C(=O)c1ccc2c(c1)nc(CNc1ccc(C#N)cc1)n2C)c1ccccn1 ; Cl]

(IV-HCl)

with hydrochloric acid and ethanol, optionally in the presence of a cosolvent; and subsequent isolation of the product obtained as a solid. In a preferred embodiment, the starting compound is the compound of formula (IV-HCl). In another preferred embodiment, the starting compound is the crystalline compound of formula (IV-HCl).

This reaction can be carried out using concentrated solutions (although not necessarily saturated) of HCl in ethanol. The ethanol may act at the same time as the only solvent and as reactive, or either may be mixed with a suitable cosolvent as, e.g. a $(C_3-C_6)$ether, such as tetrahydrofuran; a $(C_1-C_6)$ halogenated solvent, such as dichloromethane; a $(C_5-C_{12})$ alkane such as heptane; $(C_5-C_{12})$cycloalkane such as cyclohexane, or a $(C_6-C_9)$aromatic solvent, such as toluene or xylene. In a preferred embodiment, ethanol is used as the sole solvent. In another preferred embodiment, ethanol is used mixed with toluene, as this mixture of solvents offers advantages for the isolation of the product. In particular, it allows the obtention of a solid that is filtered easier, that is less sensitive to humidity, and with a better yield.

Generally, the reaction is carried out in a temperature range between 10-50° C., preferably between 30-35° C., and more preferably at 35° C. The times necessary for complete conversion are comprised between 12-48 hours, preferably between 15-30 hours.

In a more preferred embodiment of the invention, a saturated HCl solution is used in a mixture of ethanol:toluene 1:1 at 35° C.

In the case that the reaction is performed using ethanol only, a cosolvent can be added subsequently for the isolation of the imidate salt of formula (III-HCl). Examples of possible cosolvents are, e.g. $(C_3-C_6)$ethers, such as tert-butylmethyl ether, diethyl ether or tetrahydrofuran; $(C_6-C_9)$aromatic solvents, such as toluene, chlorobenzene or xylene; or $(C_1-C_6)$ halogenated solvents. Preferably, toluene is used.

Preferably, to allow an improved separation of the solid from the mother liquors, it is advisable to dilute the reaction mixture with ethanol/toluene to about 7 reaction volumes, and to stir the mixture at room temperature for several hours.

In a particular embodiment, the compound isolated is the crystalline form I of the compound (III-HCl). Said crystalline form shows an X-Ray powder diffraction pattern substantially according to FIG. 3. In another preferred embodiment, the invention relates to the crystalline form I of the compound of formula (III-HCl) that shows an X-Ray powder diffraction pattern comprising 2θ angle values at 4.7, 7.6, 11.5, 14.1, 16.6, 20.5, 22.3, 23.1, 23.9 and 26.0 measured in an X-ray diffractometer with Cu Kα radiation (1.5418 Å). The crystalline form I of the compound (III-HCl) may be obtained by a process comprising the crystallization of the compound (III-HCl) from a solution thereof in a mixture of toluene/ethanol approximately 1/1 with a concentration in HCl of between 50-100% of the saturation concentration of the toluene/ethanol mixture approximately 1/1 at 35° C.; at a temperature comprised between 0-40° C.; and in a concentration between 5-15 volumes of the ethanol/toluene mixture. Generally, the crystallized product is filtered at a temperature that may range between −20° C. and room temperature.

To induce the crystallization process that allows the isolation of the crystalline form I of the imidate salt, in case it has not taken place during the reaction, there are several options, e.g., the solution can be cooled down to 0° C. Additionally, it can be seeded to facilitate the crystallization.

The crystalline form I of the compound (III-HCl) can be converted into the amorphous form of the same compound by drying under vacuum, under a pressure between 1-10 mbar and at a temperature between 15-30° C., preferably room temperature. Thus, another aspect of the invention relates to the amorphous form of the compound (III-HCl). Said amorphous form shows an X-Ray powder diffraction pattern substantially according to FIG. 4.

The process for preparing the amorphous compound (III-HCl) by drying in the conditions described above is also part of the invention.

The compound of formula (IV) is obtained by reaction of the compound of formula (VI)

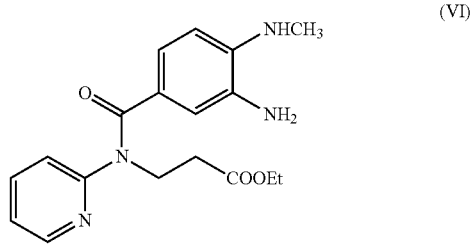 [SMILES: CCOC(=O)CCN(C(=O)c1ccc(NC)c(N)c1)c1ccccn1]

with the compound of formula (V)

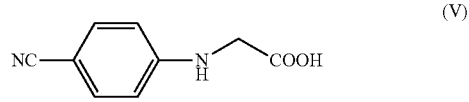 [SMILES: N#Cc1ccc(NCC(=O)O)cc1]

in the presence of a coupling agent, and subsequent cyclization with a cyclization agent.

The coupling reaction between the compound of formula (VI) and the compound of formula (V) is already known in the state of the art, e.g. in the patent application WO 98/37075. This reaction e.g. is carried out within a suitable solvent, as tetrahydrofuran, at a suitable temperature, preferably by heating. The coupling agent used is preferably 1,1'-carbonyldiimidazole, and the cyclization agent, acetic acid.

However, in the present invention, unlike the process described in document WO 98/37075, the obtained compound of formula (IV) is not purified by chromatography, but after the work-up, the corresponding hydrochloride (IV-HCl) is precipitated.

The standard precipitation process takes place within a solution of the compound of formula (IV) in a suitable solvent, at a temperature between 0-60° C., preferably between 30-40° C., by addition of HCl in pure gas form or in solution, preferably HCl in aqueous solution or in an organic solvent, and more preferably 35-37% aqueous HCl. Typically between 0.7-1.5 equivalents of HCl in relation to the starting compound (VI) are used, preferably between 1.1-1.2 equivalents.

The solvent in which the compound of formula (IV) is dissolved can be a ($C_1$-$C_6$)alcohol, such as ethanol, isopropanol or butanol; a ($C_1$-$C_6$)alkyl ($C_1$-$C_6$)ester, such as ethyl acetate, isopropyl acetate or isobutyl acetate; a ($C_3$-$C_8$)ketone, such as methylisobutylketone, methylethylketone or acetone; a ($C_3$-$C_6$)ether such as methyl tert-butyl ether, 2-methyltetrahydrofuran, or tetrahydrofuran; a ($C_1$-$C_6$)halogenated solvent, such as dichloromethane; a ($C_6$-$C_9$)aromatic solvent such as toluene or xylene; a ($C_6$-$C_{12}$)alkane such as heptane, ($C_6$-$C_{12}$)cycloalkane such as cyclohexane, or mixtures of the above. Preferably, the solvent is ($C_1$-$C_6$)alcohol, and more preferably, isopropanol.

After the appearance of the solid corresponding to the hydrochloride (IV-HCl), the reaction mixture is stirred for some time, generally between 0-3 hours, preferably 30 minutes, keeping the temperature indicated above. Subsequently, the mixture can optionally be stirred at 0° C. for some time, generally between 0-3 hours, preferably 30 minutes, and filtered. In a preferred embodiment, the reaction mixture is stirred between 30 minutes and 3 hours at room temperature and, subsequently, between 30 minutes and 3 hours at 0° C. Finally, the solid is filtered, washed and dried, obtaining compound (IV-HCl). The solid obtained can optionally be recrystallized from ethanol, obtaining the product with a higher than 99% a/a purity according to HPLC/MS.

Both the precipitated product from isopropanol and the recrystallized product from ethanol show the same crystalline structure.

As previously indicated, the conversion of the intermediate (IV) into the compound of formula (II) already described in the state of the art comprises a first step of adding HCl. Thus, although it could be considered that the compound (IV-HCl) could be present in the reaction medium during this conversion, it is not isolated at any moment in solid form, but is converted directly into the compound of formula (II).

The compound (IV-HCl) in solid form has the advantage that it is particularly easy to separate by filtration. This characteristic has a direct effect on the global yield of the process and, therefore, is especially important when the process is carried out at an industrial scale, since a product showing improved separation characteristics can be isolated faster, better washed and therefore faster dried.

Thus, another aspect of the invention relates to the compound of formula (IV-HCl), i.e. ethyl N-[(2-[(p-cyanophenyl)amino]methyl)-1-methyl-1H-benzimidazole-5-carbonyl]-N-(2-pyridyl)-3-aminopropionate hydrochloride in solid form. In a preferred embodiment, the invention relates to the compound of formula (IV-HCl) in crystalline form.

In another preferred embodiment, the invention relates to the crystalline form of the compound of formula (IV-HCl) that shows an X-Ray powder diffraction pattern substantially according to FIG. 2. In another preferred embodiment, the invention relates to the crystalline form of the compound of formula (IV-HCl) that shows an X-Ray powder diffraction pattern comprising 2θ angle values at 3.7, 10.0, 10.9, 17.7, 18.3, 20.9, 22.0, 22.5, 23.7, 25.9 and 26.4 measured in an X-ray diffractometer with Cu Kα radiation (1.5418 Å).

The process of preparing said crystalline form of the compound of formula (IV-HCl) is also part of the invention. This crystalline form may be obtained by a process that comprises reacting the compound (IV) with HCl in isopropanol or ethanol, and separating the crystallized product from the reaction medium, e.g. by filtration. Alternatively, said crystalline form may be obtained by recrystallization of the compound of formula (IV-HCl) from a solution thereof in ethanol or isopropanol, at a temperature comprised between 10-80° C., and at a concentration between 5-20 volumes of ethanol or isopropanol; preferably between 4-7 volumes of ethanol or isopropanol. Generally, the crystallized product is filtered out at a temperature that may range between 0-40° C.

Each of the process steps in the present invention represents a significant improvement in relation to the processes described and may be combined with some of the steps already known. Additionally, when the different steps in the present invention are carried out together the resulting process is a particularly effective industrializable process.

As already mentioned above, the compound of formula (II-HCl) may be converted into a compound of formula (I), wherein $R^1$ represents H and $R^2$ represents H, i.e. a compound (Ia),

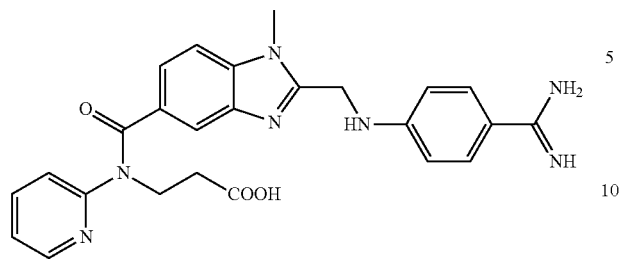
(Ia)

corresponding to dabigatran, or either into a compound of formula (I), wherein $R^1$ represents ethyl and $R^2$ represents n-hexyloxycarbonyl, wherein the n-hexyloxycarbonyl radical refers to the radical —COO—$(CH_2)_5CH_3$, i.e. a compound (Ib),

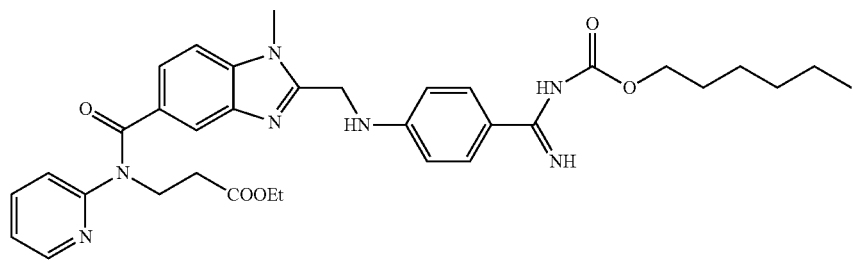
(Ib)

corresponding to dabigatran etexilate.

As already mentioned above, the preparation of the compounds of formula (I) from the compound of formula (II) is already known in the state of the art, e.g. in the patent application WO 98/37075. In a preferred embodiment, the compound of formula (I) is prepared from the crystalline form of the compound (II-HCl) indicated above.

By the process of the invention a compound of formula (I) may be obtained, wherein $R^1$ represents H and $R^2$ represents H, i.e. a compound (Ia),

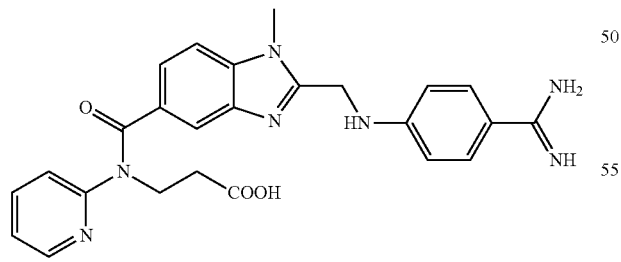
(Ia)

corresponding to dabigatran, or either a compound of formula (I), wherein $R^1$ represents ethyl and $R^2$ represents n-hexyloxycarbonyl, wherein the n-hexyloxycarbonyl radical refers to the radical —COO—$(CH_2)_5CH_3$, i.e. a compound (Ib), corresponding to dabigatran etexilate.

By way of example, the compound of formula (Ib) may be prepared by reaction of the compound of formula (II) with the compound of formula (XI)

wherein X is a halogen such as Cl or Br, preferably Cl. The reaction is carried out at a temperature between 0-50° C., preferably between 10-25° C., and optionally in the presence of a base, such as $K_2CO_3$, $Na_2CO_3$, $KHCO_3$, $NaHCO_3$, or triethylamine. In a preferred embodiment, $K_2CO_3$ is used. In another preferred embodiment, triethylamine is used. This reaction can be carried out in a ($C_3$-$C_8$)ketone-type solvent, such as acetone, or an ether-type, such as dioxane or tetrahydrofuran, optionally in the presence of water. Preferably, this reaction is carried out in tetrahydrofuran or acetone. In a preferred embodiment, acetone is used as a solvent and triethylamine as a base.

The triethylammonium salts generated in the course of the reaction can be removed by filtration or by an aqueous wash.

The compound of formula (Ia) may be prepared e.g. by reaction of the compound of formula (II) or (II-HCl) with a base, such as sodium hydroxide, in a suitable solvent, as e.g. a mixture of ethanol and water, and at a suitable temperature, e.g. room temperature.

Additionally, a compound of formula (I) may be optionally converted into a pharmaceutically acceptable salt thereof. The salts of the compound of formula (I), in particular of the compound (Ib), and the obtaining thereof have already been described, e.g. in the documents WO 03/074056, WO 2006/114415 and WO 2008/43759. In a preferred embodiment, the invention relates to the compound (Ib) methanesulfonate or mesylate, i.e. to dabigatran etexilate mesylate (Ib-MsOH). This salt is prepared from the compound (Ib) and methanesulfonic acid, e.g. in a mixture of acetone and water, and at a temperature between 20-40° C.

The solvates of the compounds of formula (I) or of its pharmaceutically acceptable salts, including hydrates, are also part of the invention. In general, the solvated forms with pharmaceutically acceptable solvents such as water, ethanol and the like are equivalent to the non-solvated forms for the purposes of the present invention.

Throughout the description and claims the word "comprises" and its variants are not intended to exclude other technical characteristics, additives, components or steps. To those skilled in the art, other objects, advantages and characteristics of the invention will be understood in part from the description and in part from the practice of the invention. The following examples and drawings are provided by way of illustration only, and are not intended to be limiting of the present invention. Further, the present invention covers all the possible combinations of particular and preferred embodiments indicated herein.

EXAMPLES

Figure 1:
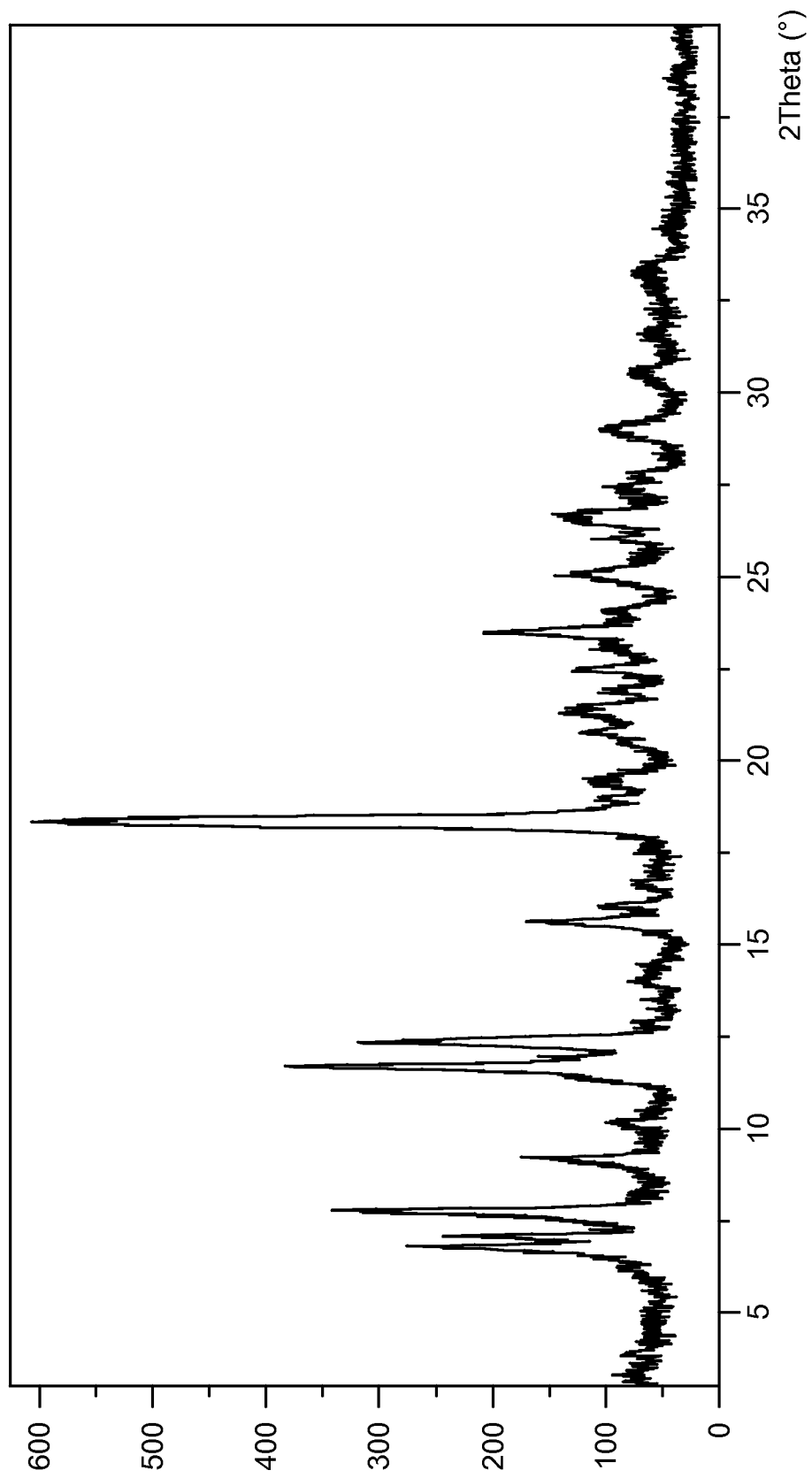
FIG. 1 shows the X-Ray powder diffraction curve (intensity (counts) vs. 2theta angle (°)) of the crystalline form of the compound of formula (II-HCl) which is a mixture of form I and II.

In the examples, the following abbreviations have been used:
EtOAc: ethyl acetate
Ar: argon
c.: concentrated
t.l.c.: thin layer chromatography DMF: dimethylformamide
EtOH: ethanol
Et₃N: triethylamine
IPA: isopropanol
PXRD: Powder X-Ray diffraction
r.t.: room temperature
THF: tetrahydrofuran DRX analysis was performed in a PANalytical X'Pert PRO MPD diffractometer with Bragg-Bentano geometry and Cu $K_\alpha$ radiation (1.5418 Å). The system was provided with a RTMS detector. Samples were grinded and placed in Si sample holders of zero background. The recording parameters were a range of 2Theta=3-40° and a total recording time of 125 s.

Example 1

Ethyl N-[(2-[(p-cyanophenyl)amino]methyl)-1-methyl-1H-benzimidazole-5-carbonyl]-N-(2-pyridyl)-3-aminopropionate hydrochloride (IV-HCl)

Under Ar atmosphere, N-(p-cyanophenyl)-glycine (V) (7.22 g, 41.0 mmol) and 1,1'-carbonyldiimidazole (6.64 g, 41.0 mmol) were suspended in anhydrous THF (315 mL). It was refluxed for 45 minutes and a solution of compound (VI) (12.74 g, 37.2 mmol) in anhydrous THF (56 mL) was added slowly. After 6 h under reflux, the reaction mixture was cooled down, and the solvent was distilled under low pressure. The oil obtained was dissolved in glacial acetic acid (155 mL) and refluxed for 1 h. The solvent was removed under low pressure, the residue was dissolved in $CH_2Cl_2$ (130 mL) and washed with $H_2O$ (2×130 mL). The organic phase was dried over anhydrous $MgSO_4$ and the solvent was distilled under low pressure. The residue obtained was dried under vacuum, obtaining 20.19 g of crude (IV) (75% a/a purity according to HPLC/MS).

The brown oil was dissolved in isopropanol (101 mL) at 35° C. and HCl(c) (37%, 3.40 mL, 41.1 mmol) was added slowly. After a short time an abundant white solid appeared. It was stirred at 35° C. for 30 min and next at 0° C. for 30 min. The solid was filtered out, washed with IPA (15 mL) and dried under vacuum, obtaining the product (IV-HCl) (14.25 g, 74% yield, 97% a/a purity according to HPLC/MS). This solid was recrystallized from EtOH (160 mL), washed with EtOH (2×10 mL) and dried under vacuum, obtaining 12.13 g (23.4 mmol, 63% global yield, 99% a/a purity according to HPLC/MS) of the product (IV-HCl).

¹H RMN (400 MHz, CD₃OD): δ (ppm)=8.33 (ddd, J=4.8, 2.0, 0.8, 1H), 7.77 (d, J=8.8, 1H), 7.66 (dd, J=1.6, 0.8, 1H), 7.60 (ddd, J=8.0, 8.0, 2.0, 1H), 7.55-7.50 (m, 3H), 7.17 (ddd, J=7.6, 4.8, 0.8, 1H), 7.09 (d, J=8.0, 1H), 6.83 (d, J=8.8, 2H), 5.02 (s, 2H), 4.34 (t, J=7.2, 2H), 4.05 (q, J=7.2, 2H), 4.02 (s, 3H), 2.76 (t, J=7.2, 2H), 1.19 (t, J=7.2, 3H).

Melting point ($T_{melt}$): 213-215° C.

Figure 2:
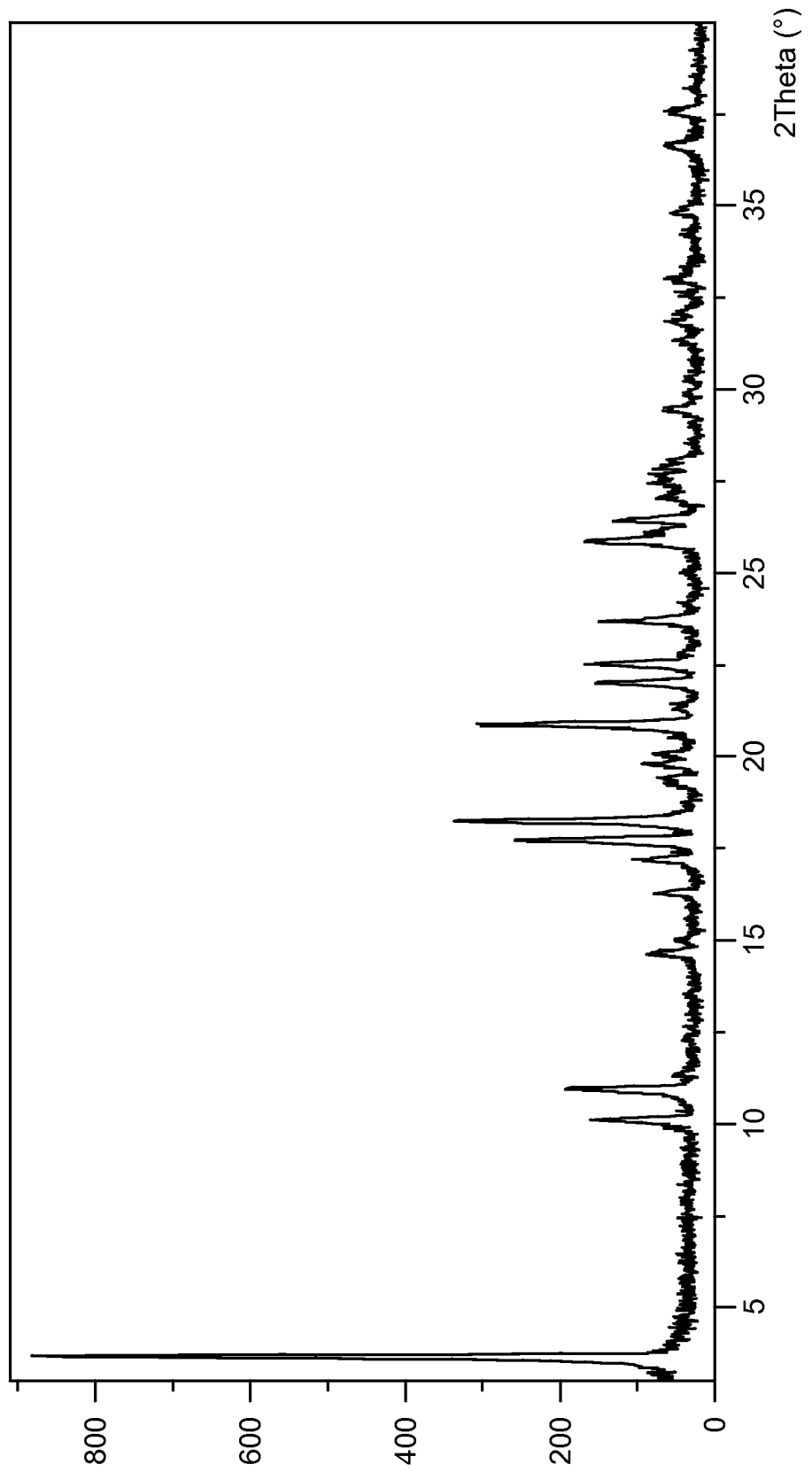
FIG. 2 shows the X-Ray powder diffraction curve (intensity (counts) vs. 2theta angle (°)) of the crystalline form of the compound of formula (IV-HCl).

PXRD: FIG. 2, 2theta angle values (°)=3.7, 10.0, 10.9, 17.7, 18.3, 20.9, 22.0, 22.5, 23.7, 25.9, 26.4.

Example 2

Ethyl N-[(2-[(p-[ethoxyimidoyl]phenyl)amino]methyl)-1-methyl-1H-benzimidazole-5-carbonyl]-N-(2-pyridyl)-3-aminopropionate hydrochloride (III-HCl)

a) Reaction Using EtOH as Solvent, Crystallization of the Product by Addition of Toluene The hydrochloride (IV-HCl) (2.12 g, 4.08 mmol) was stirred in a saturated HCl solution in EtOH (3.8 mL) at 30° C. for 24 h. The mixture obtained was diluted with EtOH (3.8 mL) and toluene (7.6 mL) was added. It was stirred at r.t. for 2 h 30 min, subsequently at 0° C. for 15 min, the crystalline solid was filtered out under a nitrogen atmosphere, washed with cold toluene:EtOH 1:1 (2 mL) and dried under vacuum at room temperature, obtaining the amorphous imidate hydrochloride (2.05 g, 89% yield, 86% a/a purity according to HPLC/MS).

b) Reaction Performed in EtOH:Toluene 1:1, Direct Crystallization of the Product in the Reaction Medium In a pressure reactor the hydrochloride (IV-HCl) (2.34 g, 4.51 mmol) was stirred in a saturated HCl solution in EtOH: toluene 1:1 (11.6 mL) at 30° C. for 26 h and next at 35° C. for 17 h. The mixture was cooled down, diluted with EtOH: toluene 1:1 (4.6 mL), seeded with newly obtained product and stirred at r.t. for 3 h. The crystalline solid was filtered out under a nitrogen atmosphere and dried under vacuum at room temperature, obtaining the amorphous imidate hydrochloride (2.03 g, 80% yield, 85% purity according to HPLC/MS).

¹H RMN (400 MHz, CD₃OD): δ (ppm)=8.36 (ddd, J=5.6, 2.8, 0.8, 1H), 7.93 (d, J=8.8, 1H), 7.79 (dd, J=8.8, 0.8, 1H), 7.75-7.70 (m, 2H), 7.54 (dd, J=8.8, 1.6, 1H), 7.25 (ddd, J=7.6, 5.2, 0.8, 1H), 7.22 (d, J=8.0, 1H), 6.94 (d, J=8.8, 2H), 5.12 (s, 2H), 4.55 (q, J=6.8, 2H), 4.34 (t, J=6.8, 2H), 4.04 (q, J=6.8, 2H), 4.04 (bs, 3H), 2.77 (t, J=6.8, 2H), 1.57 (t, J=6.8, 3H), 1.18 (t, J=6.8, 3H).

Figure 3:
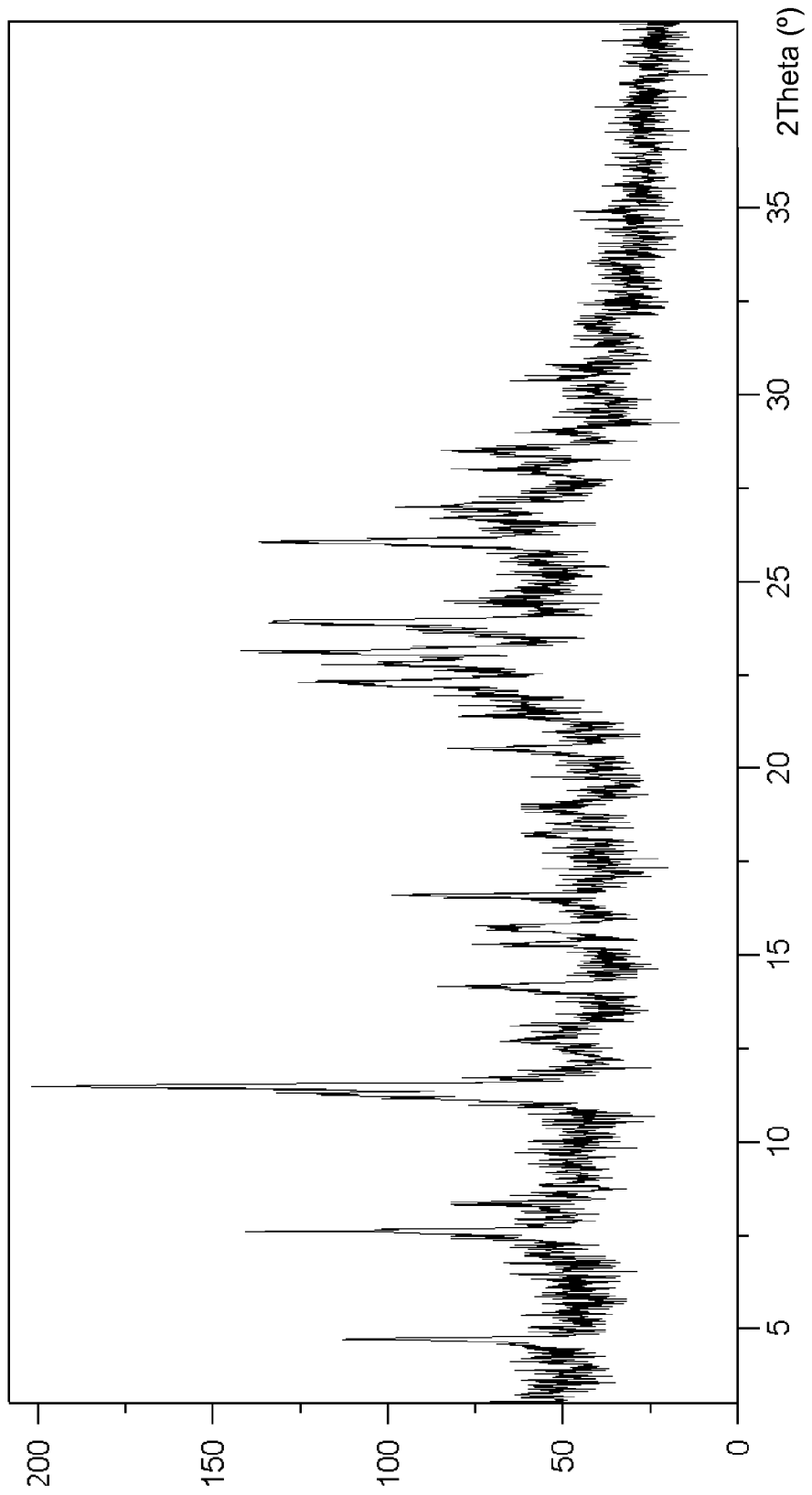
FIG. 3 shows the X-Ray powder diffraction curve (intensity (counts) vs. 2theta angle (°)) of the crystalline form I of the compound of formula (III-HCl).
Figure 4:
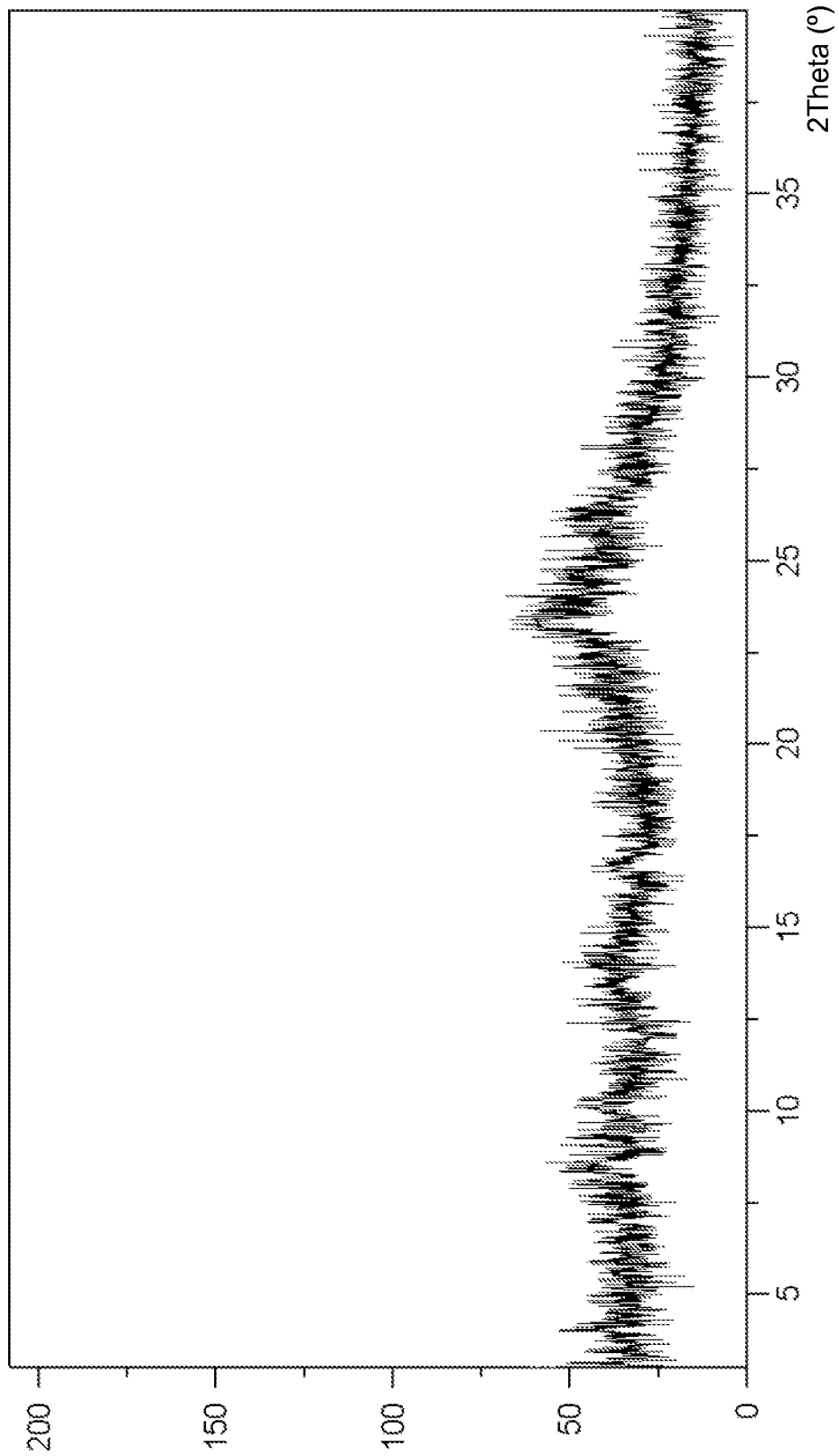
FIG. 4 shows the X-Ray powder diffraction curve (intensity (counts) vs. 2theta angle (°)) of the amorphous form of the compound of formula (III-HCl).
Figure 5:
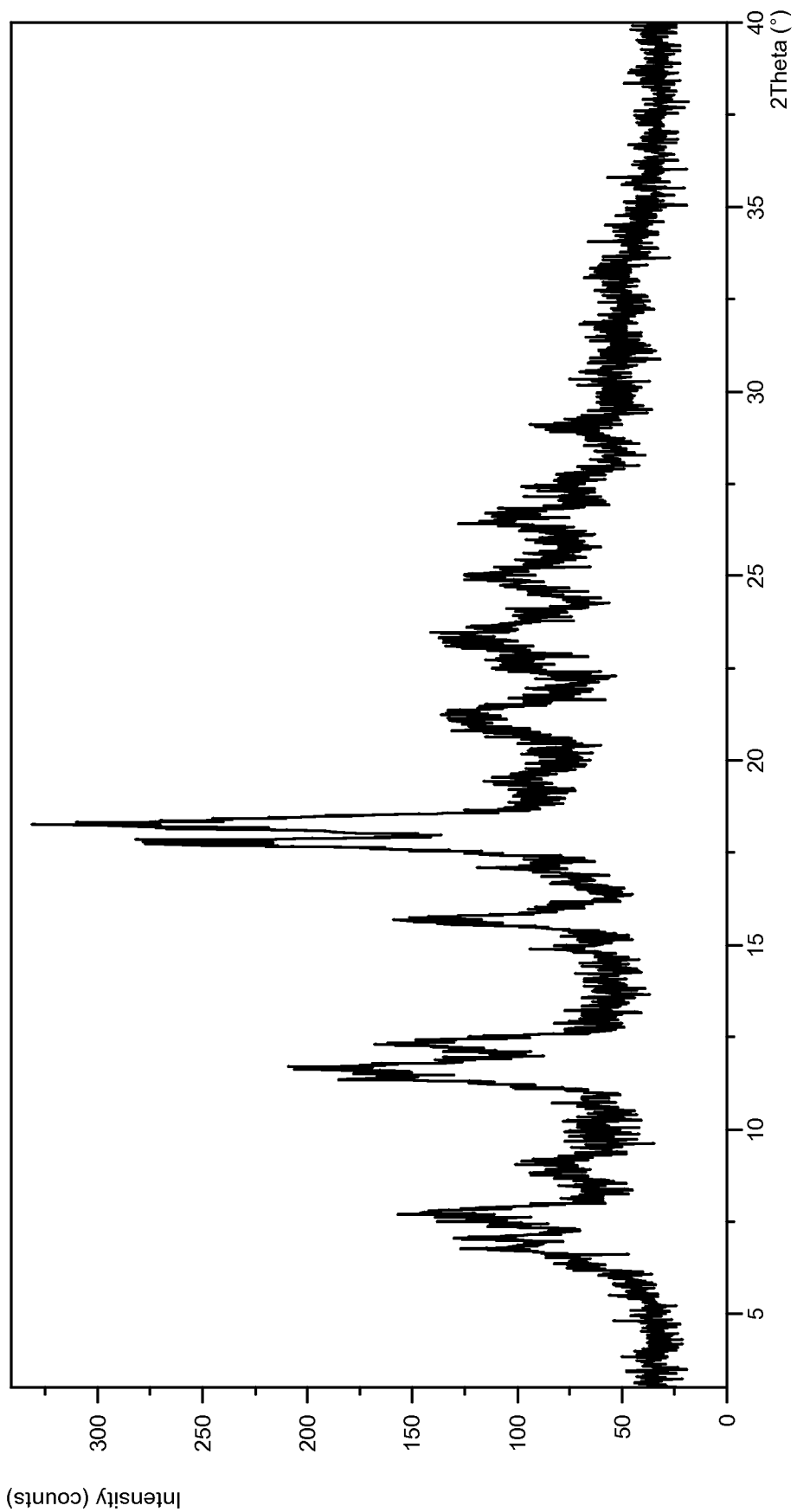
FIG. 5 shows the X-Ray powder diffraction curve (intensity (counts) vs. 2theta angle (°)) of a mixture of form I, form II and form IV of the compound of formula (II-HCl).

PXRD crystalline intermediate: FIG. 3, 2theta angle values (°)=4.7, 7.6, 11.5, 14.1, 16.6, 20.5, 22.3, 23.1, 23.9, 26.0.

Example 3

Ethyl N-([([amidino)phenyl]amino)methyl]-1-methyl-1H-benzimidazole-5-carbonyl)-N-(2-pyridyl)-3-aminopropionate hydrochloride (II-HCl)

a) Reaction Using $(NH_4)_2CO_3$

Figure 11:
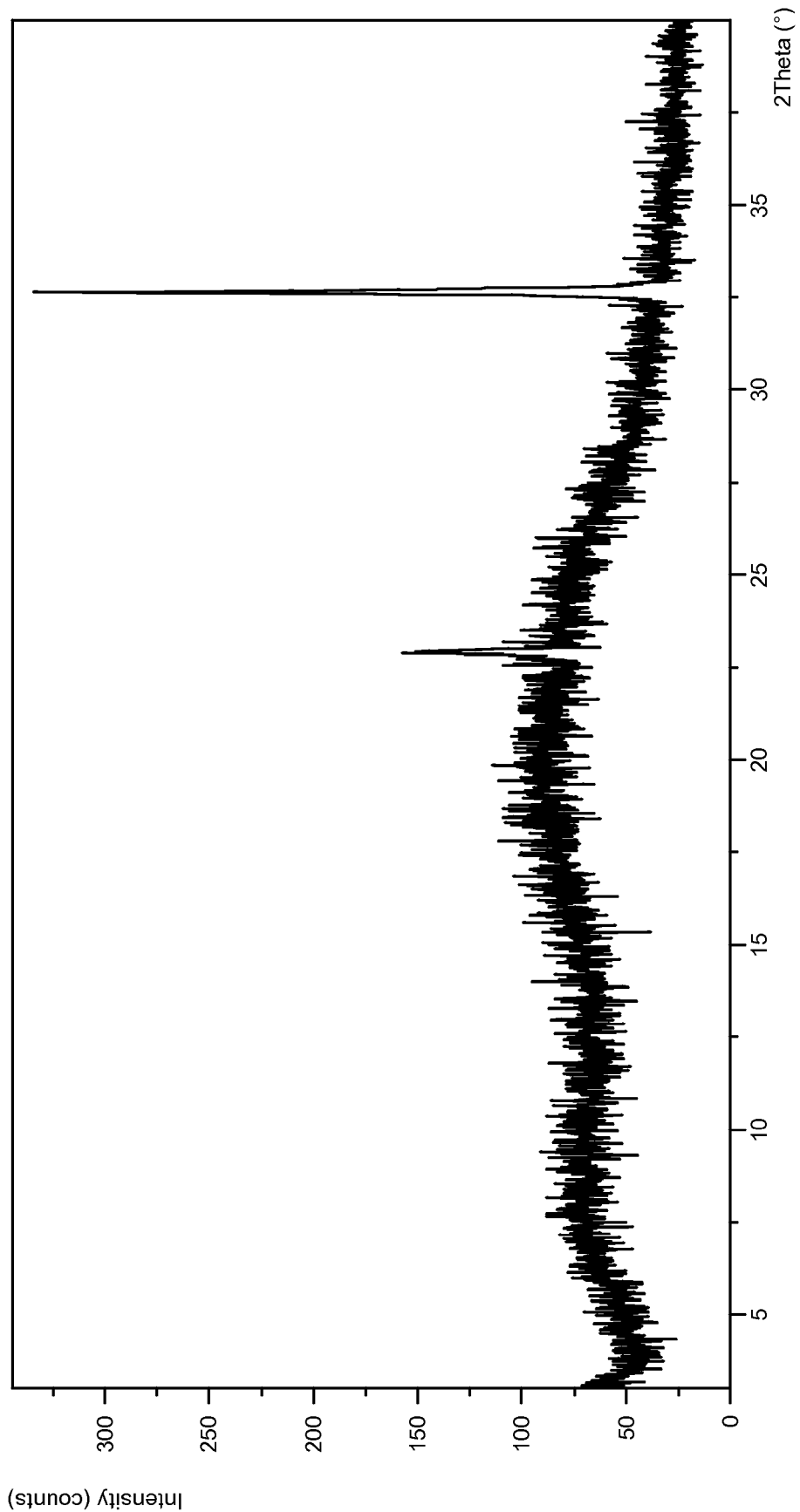
FIG. 11 shows the X-Ray powder diffraction curve (intensity (counts) vs. 2theta angle (°)) of the amorphous form of the compound of formula (II-HCl) slightly unpurified with ammonium chloride.

Under Ar atmosphere, $(NH_4)_2CO_3$ (1.05 g, 10.93 mmol) was suspended in EtOH (20 mL). It was stirred at r.t. for 40 min and a solution of the imidate salt (III-HCl) (2.06 g, 3.64 mmol, >90% a/a purity according to HPLC/MS) was added in EtOH (12 mL). It was stirred at r.t. overnight, the solid was filtered out, washed with EtOH (2 mL) and the filtrates were distilled under low pressure, at a temperature of 55° C., to a volume of approximately 10 mL. Toluene (25 mL) was added and 25 mL of the solvent were distilled under low pressure, at a temperature of 60-65° C.; this operation was performed twice. The suspension obtained was cooled down, the solid was filtered out, washed with toluene (1 mL) and dried under vacuum, obtaining the amidino compound hydrochloride (II-HCl) in amorphous form (1.69 g, 82% yield, 93% a/a purity according to HPLC/MS, cf. FIG. 11).

b) Reaction Using a $NH_3$ Solution in EtOH

Under Ar atmosphere, the imidate salt (III-HCl) (7.15 g, 12.65 mmol, 94% purity according to HPLC/MS) was dissolved in EtOH (51 mL). A $NH_3$ solution in EtOH (2.0 M, 20 mL, 40.0 mmol) was added slowly and stirred at r.t. for 48 h. EtOH was distilled under low pressure (approximately 35 mL), the reaction mixture was cooled down, the solid was filtered out and washed with EtOH (7 mL). The filtrates were mixed and distilled again under low pressure to a volume of approximately 14 mL. Toluene (56 mL) was added, and the same amount of solvent was distilled under low pressure; this operation was performed twice. It was left to cool down, the solid was filtered out, washed with toluene (7 mL) and dried under vacuum, obtaining the amorphous crude hydrochloride (II-HCl) (6.63 g, 98% yield, 92% a/a purity according to HPLC/MS). The hydrochloride was recrystallized from IPA (86 mL), cold filtered and washed with cold IPA (13 mL). The solid was dried under vacuum, obtaining the product of interest (4.75 g, 70% yield from the imidate salt, higher than 99% a/a purity according to HPLC/MS).

$^1$H RMN (400 MHz, CD$_3$OD): δ (ppm)=8.39 (m, 1H), 7.63-7.58 (m, 3H), 7.51 (ddd, J=8.0, 8.0, 2.0, 1H), 7.38 (d, J=8.4, 1H), 7.29 (dd, J=8.8, 1.6, 1H), 7.15-7.12 (m, 1H), 6.93 (d, J=8.0, 1H), 6.86 (d, J=8.8, 2H), 4.70 (s, 2H), 4.36 (t, J=7.2, 2H), 4.05 (q, J=7.2, 2H), 3.83 (s, 3H), 2.76 (t, J=7.2, 2H), 1.20 (t, J=7.2, 3H).

PXRD: FIG. 1, 2theta angle values (°)=6.8, 7.1, 7.8, 9.2, 11.7, 12.3, 15.6, 18.4, 23.5.

Example 4

Ethyl N-[([([N-hexyloxycarbonyl)amidino]phenyl)amino]methyl)-1-methyl-1H-benzimidazole-5-carbonyl]-N-(2-pyridyl)-3-aminopropionate (Ib)

a) Reaction Using THF as Solvent

Under Ar atmosphere, the amidino compound hydrochloride (II-HCl) (1.70 g, 3.17 mmol, 92% a/a purity according to HPLC/MS) was stirred in anhydrous THF (30 mL), cooled down to 0° C. and Et$_3$N (1.35 mL, 9.68 mmol) and n-hexyl chloroformate (0.65 mL, 3.98 mmol) were added, and stirred at r.t. for 1 h. After verifying the progress of the reaction by t.l.c, more n-hexyl chloroformate (0.20 mL, 1.22 mmol) and anhydrous THF (5 mL) were added and stirred at r.t. for 2 h. The solid was filtered out and the solvent was evaporated under low pressure. The residue was dissolved in EtOAc (30 mL) and the organic phase was washed with NaOH 1 N (10 mL). The aqueous phase was extracted with EtOAc (2×10 mL), the organic phases were mixed, washed with NaCl(sat) (10 mL) and dried over anhydrous MgSO$_4$. The solvent was evaporated to dryness, obtaining the crude product of interest (1.81 g, 94% yield, 86% purity according to HPLC/MS).

b) Reaction Using Acetone as Solvent

Under Ar atmosphere, the amidino compound hydrochloride (II-HCl) (1.50 g, 2.80 mmol, 100% a/a purity according to HPLC/MS) was stirred in acetone (38 mL), cooled down to 0° C. and Et$_3$N (1.17 mL, 8.40 mmol) and n-hexyl chloroformate (0.50 mL, 3.06 mmol) were added, and stirred at r.t. for 30 min. After verifying the progress of the reaction by t.l.c, more n-hexyl chloroformate (0.30 mL, 1.84 mmol) was added and stirred at r.t. for 1 h. The solvent was evaporated under low pressure and the residue was dissolved in EtOAc (30 mL), and the organic phase was washed with NaOH 1 N (15 mL). The aqueous phase was extracted with EtOAc (30 mL), the organic phases were mixed, and washed with NaCl (sat) (15 mL). The organic phase was dried over anhydrous MgSO$_4$, the solvent was evaporated to dryness and the residue obtained was dried under vacuum, obtaining the crude product of interest (1.56 g, 89% yield, 97% a/a purity according to HPLC/MS).

$^1$H RMN (400 MHz, CD$_3$OD): δ (ppm)=8.39 (dd, J=4.8, 1.2, 1H), 7.70 (d, J=8.8, 2H), 7.57 (d, J=0.8, 1H), 7.51 (ddd, J=8.0, 8.0, 1.6, 1H), 7.37 (d, J=8.4, 1H), 7.29 (dd, J=8.4, 1.6, 1H), 7.14 (m, 1H), 6.92 (d, J=8.0, 2H), 6.76 (d, J=8.8, 2H), 4.65 (s, 2H), 4.36 (t, J=7.2, 2H), 4.09 (t, J=6.8, 2H), 4.05 (q, J=7.2, 2H), 3.82 (s, 3H), 2.76 (t, J=7.2, 2H), 1.68 (m, 2H), 1.46-1.30 (m, 6H), 1.20 (m, J=7.2, 3H), 0.92 (t, J=6.8, 3H).

Example 5

Figure 6:
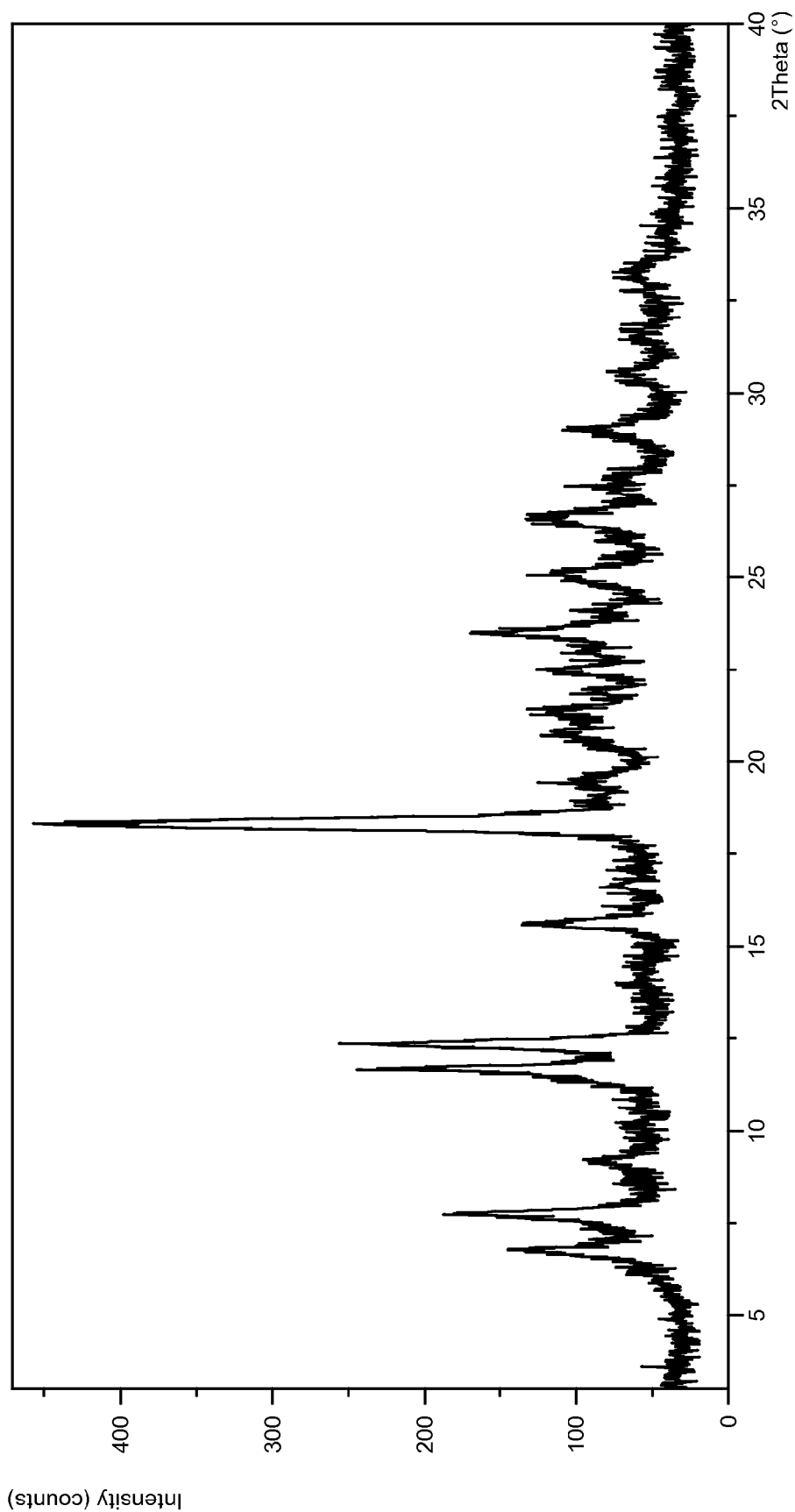
FIG. 6 shows the X-Ray powder diffraction curve (intensity (counts) vs. 2theta angle (°)) of the form I of the compound of formula (II-HCl).

Ethyl N-([([(amidino)phenyl]amino)methyl]-1-methyl-1H-benzimidazole-5-carbonyl)-N-(2-pyridyl)-3-aminopropionate hydrochloride (II-HCl) form I The product II•HCl (0.50 g) in the form of a mixture of forms I, II and IV obtained as in Example 10 was dried in a vacuum oven at 65° C. overnight. The product II•HCl (0.50 g) was obtained in form I essentially free from other crystalline forms (FIG. 6)

Example 6

Figure 7:
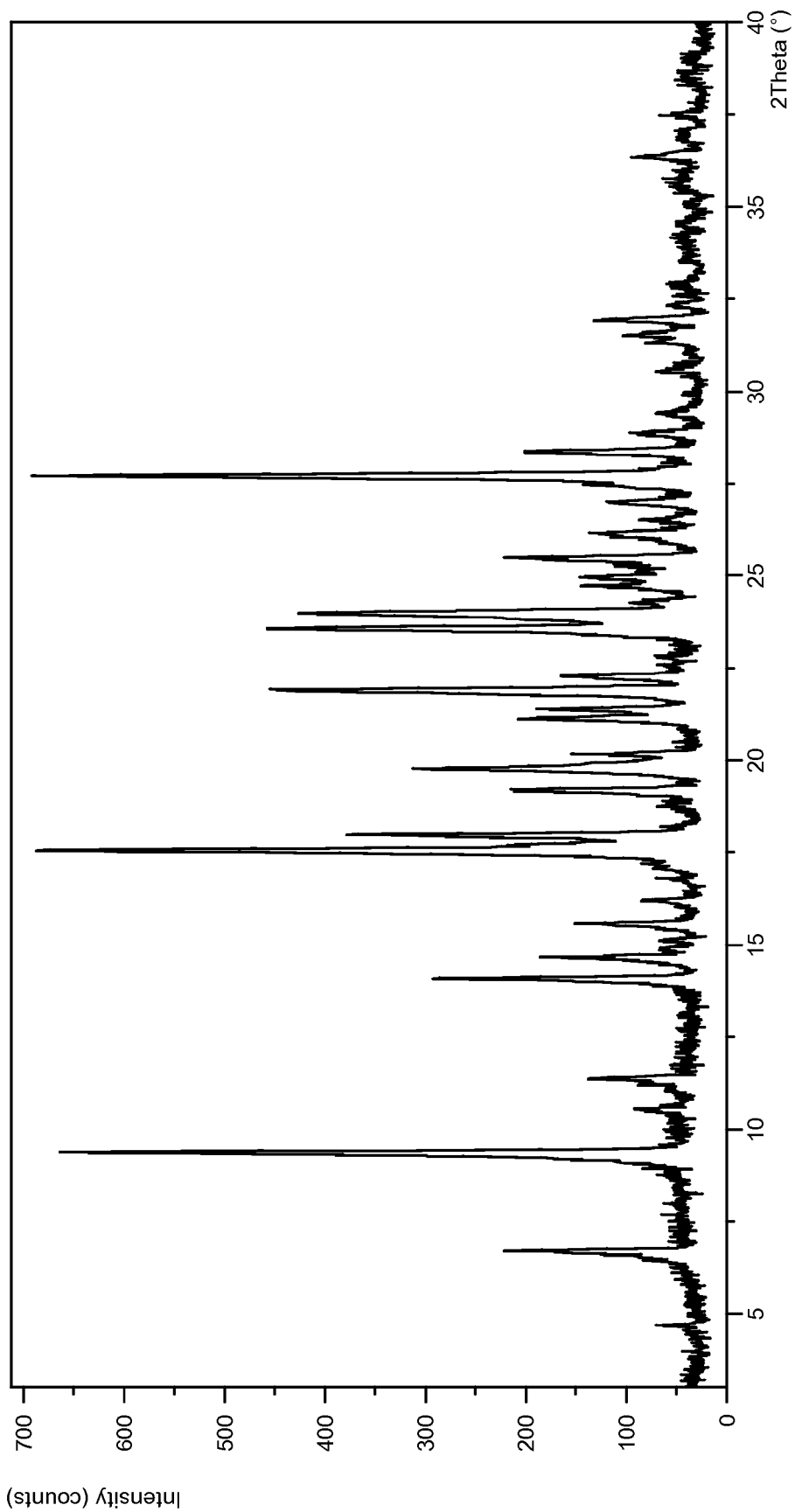
FIG. 7 shows the X-Ray powder diffraction curve (intensity (counts) vs. 2theta angle (°)) of the form V of the compound of formula (II-HCl).

Ethyl N-([([(amidino)phenyl]amino)methyl]-1-methyl-1H-benzimidazole-5-carbonyl)-N-(2-pyridyl)-3-aminopropionate hydrochloride (II-HCl) form V The product II•HCl (3.69 g, form I) obtained as in Example 5 was suspended in IPA (30 mL) and the mixture was heated to boiling. More IPA (19 mL) was added. The mixture was allowed to chill at r.t. and was stirred in a water/ice bath for 1 hour. The solid was filtered out, washed with cold IPA (4 mL) and dried in a vacuum oven at 65° C. overnight. The product II•HCl (3.28 g) was obtained in form V essentially free from other crystalline forms (FIG. 7).

Example 7

Ethyl N-([([(amidino)phenyl]amino)methyl]-1-methyl-1H-benzimidazole-5-carbonyl)-N-(2-pyridyl)-3-aminopropionate hydrochloride (II-HCl) form I The product II•HCl (4.00 g, form V) obtained as in Example 6 was suspended in $^t$BuOH (44 mL). 9 mL of solvent were distilled under atmosphere pressure and the solution was allowed to cool down, observing the appearance of a solid at 71° C. After letting it cool down to 40° C., the mixture was stirred in a water/ice bath for 1 hour. The solid was filtered out, washed with cold $^t$BuOH (8 mL) and dried in a vacuum oven at 85° C. overnight. Form IV of the compound II•HCl was obtained. A portion of the solid (1.60 g) was further dried in a vacuum oven at 85° C. for 5 more days, obtaining the product II•HCl (1.41 g) in form I essentially free from other crystalline forms.

Example 8

Figure 9:
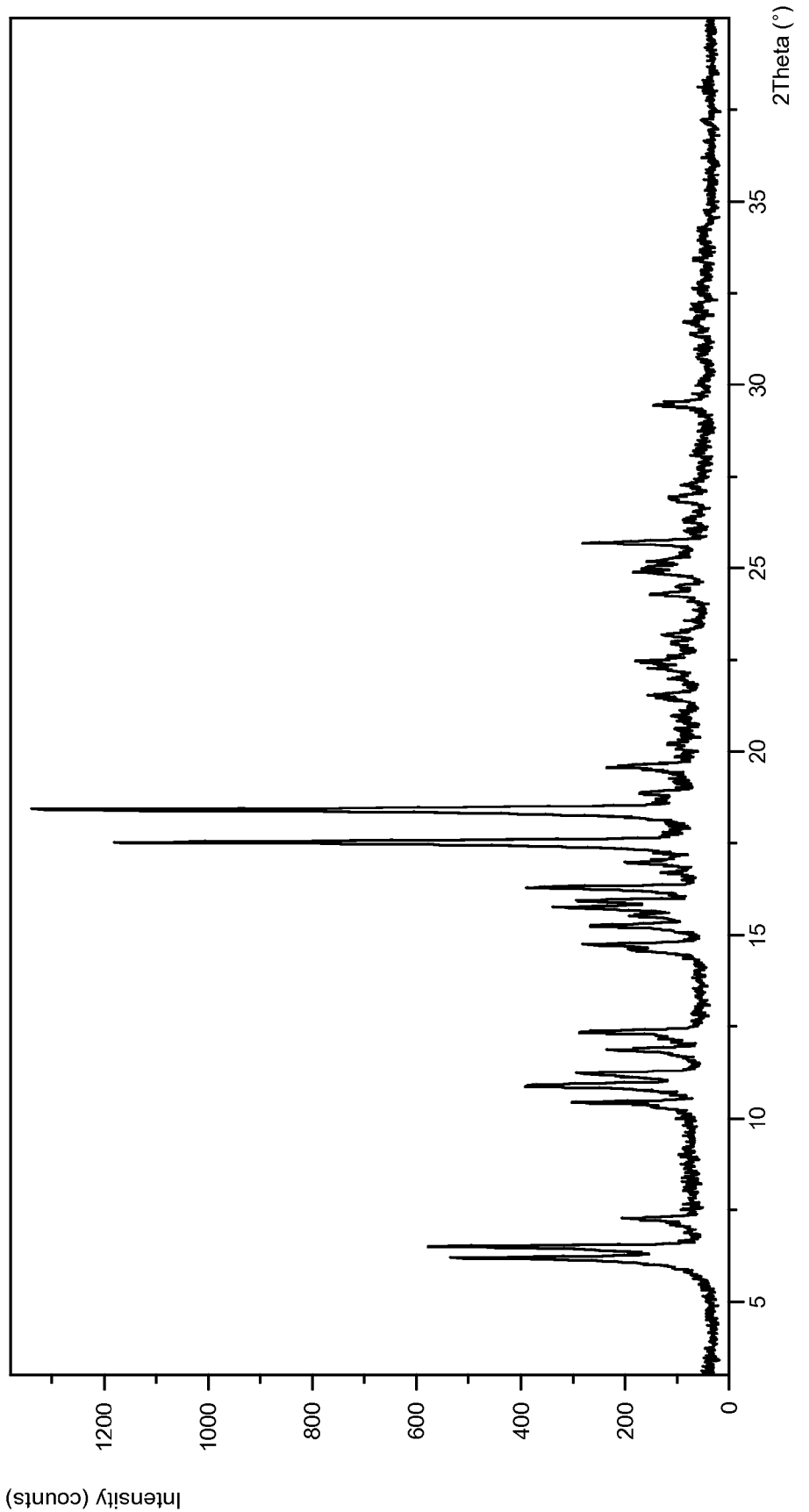
FIG. 9 shows the X-Ray powder diffraction curve (intensity (counts) vs. 2theta angle (°)) of the form III of the compound of formula (II-HCl).
Figure 10:
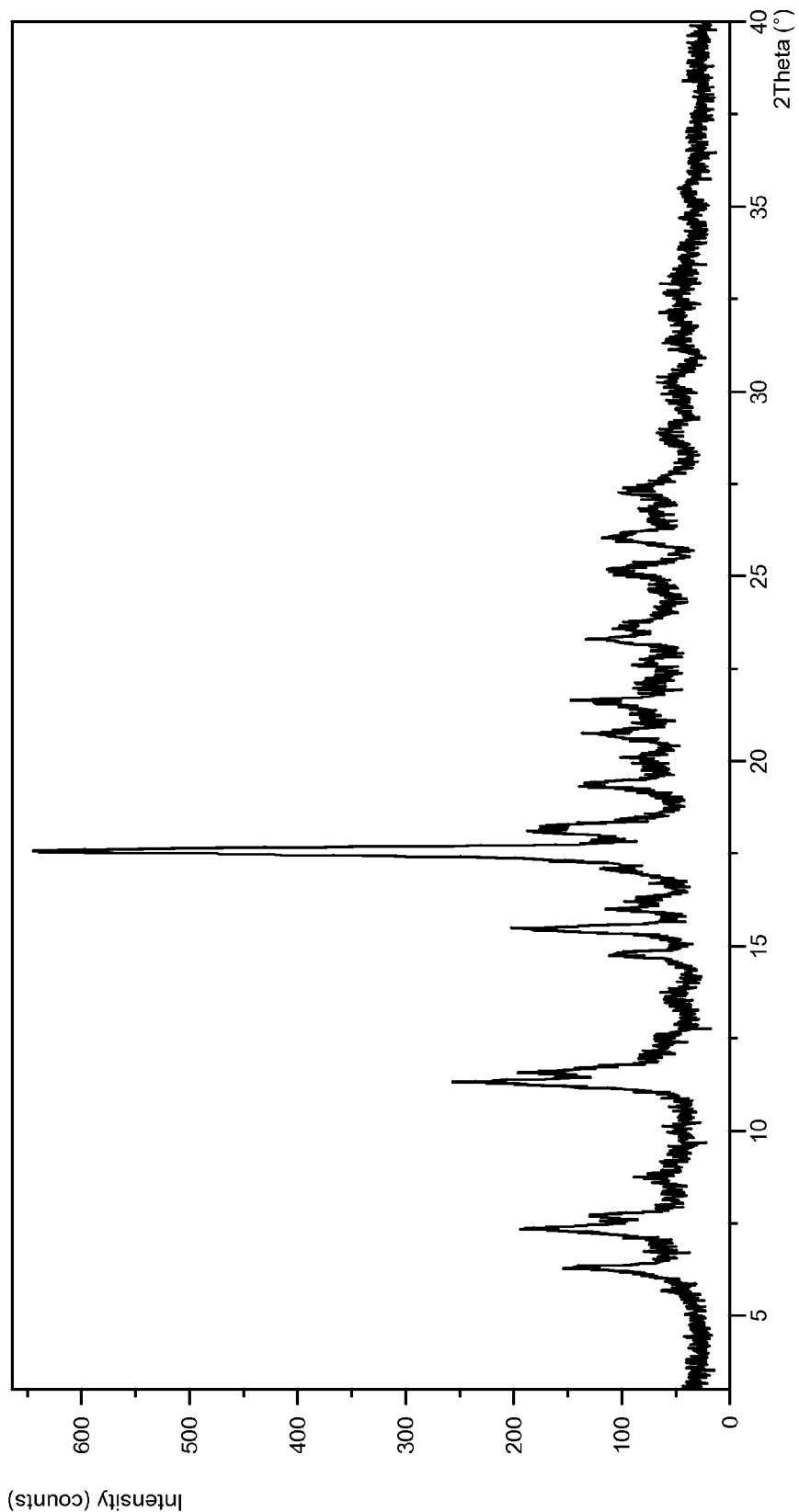
FIG. 10 shows the X-Ray powder diffraction curve (intensity (counts) vs. 2theta angle (°)) of the form IV of the compound of formula (II-HCl).

Ethyl N-([([(amidino)phenyl]amino)methyl]-1-methyl-1H-benzimidazole-5-carbonyl)-N-(2-pyridyl)-3-aminopropionate hydrochloride (II-HCl) form III II-HCl (5.00 g) was suspended in IPA (40 mL) and the mixture was heated until complete dissolution of the solid. The solution was left to cool down, observing the formation of a solid at 63° C., and the mixture was stirred at 30° C. overnight. The solid was filtered out at r.t, washed with cold IPA (5 mL) and the wet solid was analyzed by X-ray diffraction, obtaining the diffractogram showed in FIG. 9 (form III).

Example 9

Figure 8:
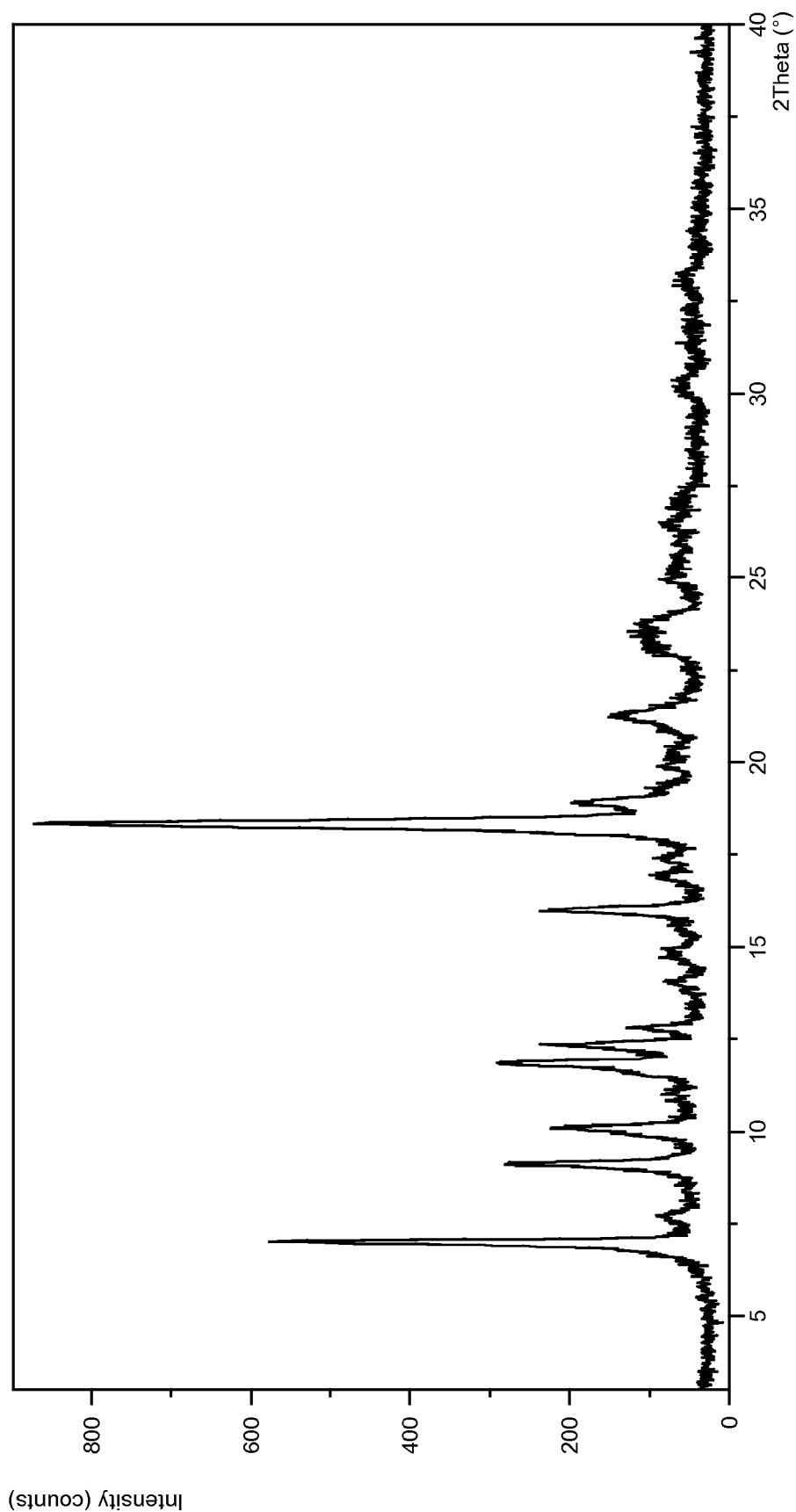
FIG. 8 shows the X-Ray powder diffraction curve (intensity (counts) vs. 2theta angle (°)) of the form II of the compound of formula (II-HCl).

Ethyl N-([([(amidino)phenyl]amino)methyl]-1-methyl-1H-benzimidazole-5-carbonyl)-N-(2-pyridyl)-3-aminopropionate hydrochloride (II-HCl) form II The wet solid of Example 8 was maintained at r.t. and in contact with the atmosphere, and it was reanalyzed 3 days later, obtaining the diffractogram showed in FIG. 8 (form II).

Example 10

Ethyl N-([([(amidino)phenyl]amino)methyl]-1-methyl-1H-benzimidazole-5-carbonyl)-N-(2-pyridyl)-3-aminopropionate hydrochloride (II-HCl) mixture of forms I, II and IV The wet solid of Example 8 was dried at r.t. under vacuum during three days and it was analyzed by X-ray diffraction, obtaining the diffractogram as the one showed in FIG. 5 (mixture of forms I, II and IV).

The invention claimed is:

1. A process of preparing a compound of formula (I), or a pharmaceutically acceptable salt thereof,

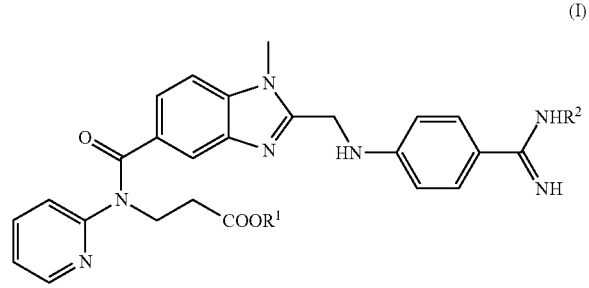
(I)

wherein $R^1$ and $R^2$ represent H; or either $R^1$ represents ethyl and $R^2$ represents n-hexyloxycarbonyl, comprising:

a) providing the compound of formula (III-HCl) as a solid;

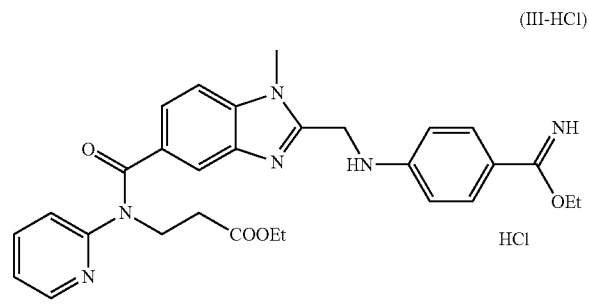 [SMILES: CCOC(=N)c1ccc(NCc2nc3cc(C(=O)N(CCC(=O)OCC)c4ccccn4)ccc3n2C)cc1 ; Cl]
(III-HCl)

b) reacting the compound of formula (III-HCl) with an amount comprised between 3-5 mol of ammonia or of an ammonium salt for each mol of the compound of formula (III-HCl) to obtain the compound of formula (II-HCl);

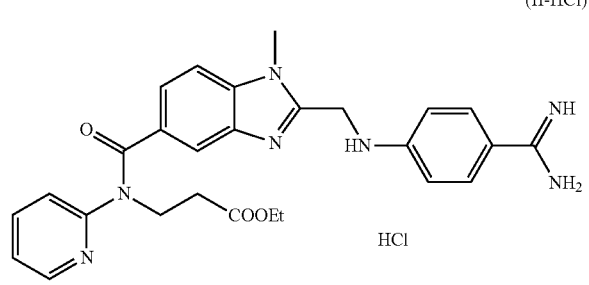
(II-HCl)

and isolating the product obtained as a solid;

c) converting the compound of formula (II-HCl) obtained into a compound of formula (I); wherein the conversion comprises reacting the compound of formula (II-HCl) with a base in a solvent, to give a compound of formula (I) wherein $R^1$ and $R^2$ represent H; or alternatively, the conversion comprises reacting the compound of formula (II-HCl) with a compound of formula (XI)

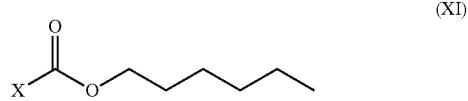
(XI)

wherein X is a halogen, optionally in the presence of a base, to give a compound of formula (I) wherein $R^1$ represents ethyl and $R^2$ represents n-hexyloxycarbonyl; and d) optionally converting the compound of formula (I) into a pharmaceutically acceptable salt thereof by treatment with an acid, or either converting a pharmaceutically acceptable salt of the compound of formula (I) into a compound of formula (I) by treatment with a base, or either converting a salt of the compound of formula (I) into another salt of the compound of formula (I) by ion exchange.

2. The process according to claim 1, wherein an ammonia solution in an organic solvent is used.

3. The process according to claim 1, wherein the compound of formula (IV)

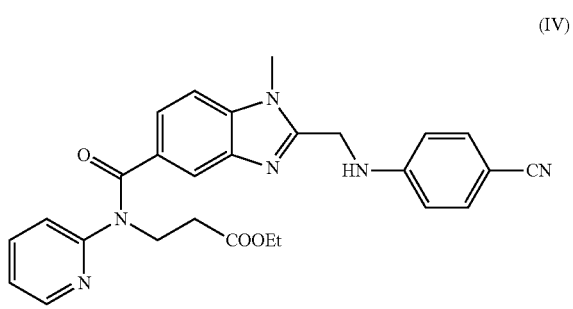 [SMILES: CCOC(=O)CCN(C(=O)c1ccc2c(c1)nc(CNc1ccc(C#N)cc1)n2C)c1ccccn1]
(IV)

or its corresponding hydrochloride (IV-HCl)

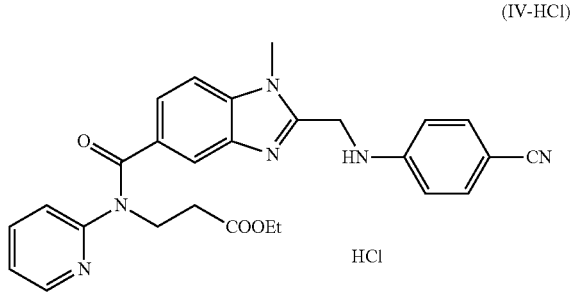 [SMILES: CCOC(=O)CCN(C(=O)c1ccc2c(c1)nc(CNc1ccc(C#N)cc1)n2C)c1ccccn1 ; Cl]
(IV-HCl)

is previously reacted with hydrochloric acid and ethanol, optionally in the presence of a cosolvent, to yield the compound of formula (III-HCl), and isolating the product obtained as a solid.

4. The process according to claim 3, wherein the starting compound is the compound of formula (IV-HCl).

5. The process according to claim 4, wherein one or more of:

the starting compound is the crystalline compound of formula (IV-HCl);

wherein the cosolvent is toluene; and, the reaction is carried out in a temperature range between 30-35° C.

6. The process according to claim 3, wherein previously:
(i) the compound of formula (VI)

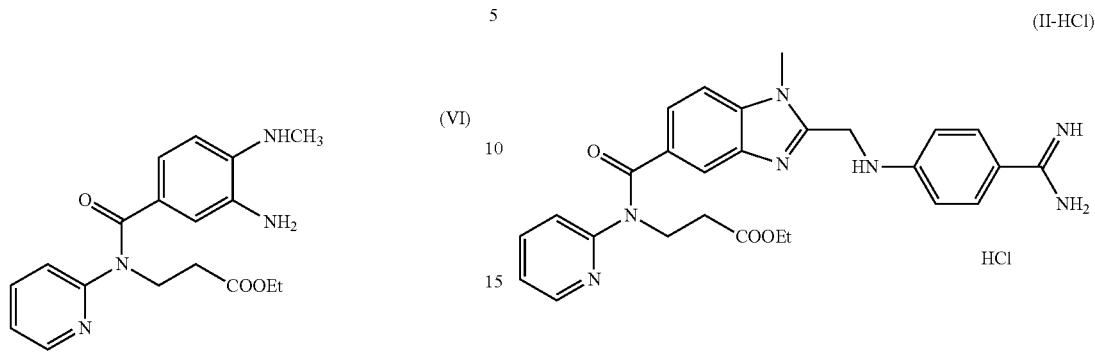

is reacted with the compound of formula (V)

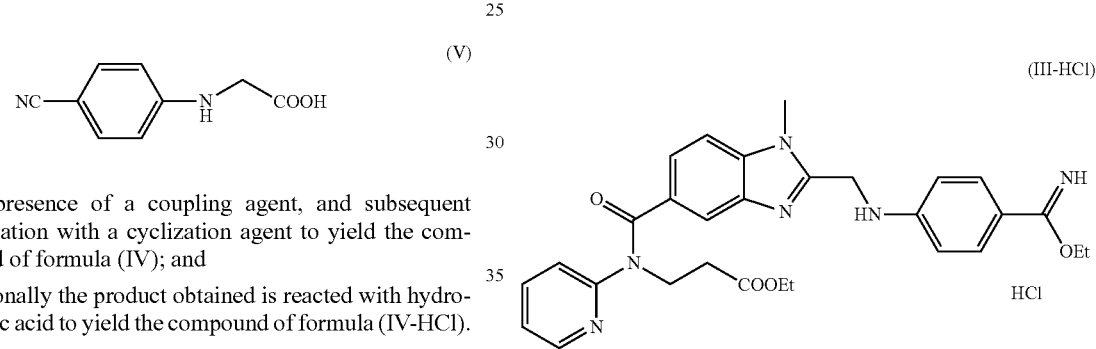

in the presence of a coupling agent, and subsequent cyclization with a cyclization agent to yield the compound of formula (IV); and (ii) optionally the product obtained is reacted with hydrochloric acid to yield the compound of formula (IV-HCl).

7. The process according to claim 6, wherein the compound of formula (IV-HCl) is isolated as a solid.

8. A compound of formula (II-HCl) as defined in claim 1, which is in a crystalline form essentially free from other crystalline forms, that shows an X-Ray powder diffraction pattern comprising 2θ angle values at 6.8, 7.8, 9.2, 11.7, 12.3, 15.6, 18.4 and 23.5 measured in an X-ray diffractometer with Cu Kα radiation (1.5418 Å).

9. A compound of formula (II-HCl) as defined in claim 1, which is in a crystalline form that shows an X-Ray powder diffraction pattern comprising 2θ angle values at 6.8, 7.1, 7.8, 9.2, 11.7, 12.3, 15.6, 18.4 and 23.5 measured in an X-ray diffractometer with Cu Kα radiation (1.5418 Å).

10. A compound of formula (II-HCl) as defined in claim 1, which is in a crystalline form essentially free from other crystalline forms, that shows an X-Ray powder diffraction pattern comprising 2θ angle values at 6.7, 9.4, 14.1, 17.6, 18.0, 19.8, 21.9, 23.6, 24.0 and 27.7 measured in an X-ray diffractometer with Cu Kα radiation (1.5418 Å).

11. A compound of formula (III-HCl) as defined in claim 1, which is amorphous.

12. A compound of formula (IV-HCl) as defined in claim 3, which is in a crystalline form that shows an X-Ray powder diffraction pattern comprising 2θ angle values at 3.7, 10.0, 10.9, 17.7, 18.3, 20.9, 22.0, 22.5, 23.7, 25.9 and 26.4 measured in an X-ray diffractometer with Cu Kα radiation (1.5418 Å).

13. A process of preparing the compound of formula (II-HCl) in solid form (II-HCl)

[structure of compound II-HCl]

comprising:
a) providing the compound of formula (III-HCl) as a solid; and (III-HCl)

[structure of compound III-HCl]

b) reacting the compound of formula (III-HCl) with an amount comprised between 3-5 mol of ammonia or of an ammonium salt for each mol of the compound of formula (III-HCl) to obtain the compound of formula (II-HCl); and isolating the product obtained as a solid.

14. A process of preparing the compound of formula (III-HCl) as defined in claim 1, in solid form comprising, reacting the compound of formula (IV)

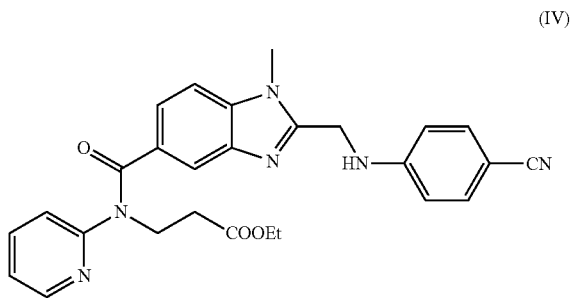 [SMILES: CCOC(=O)CCN(C(=O)c1ccc2c(c1)nc(CNc1ccc(C#N)cc1)n2C)c1ccccn1]

or its corresponding hydrochloride (IV-HCl)

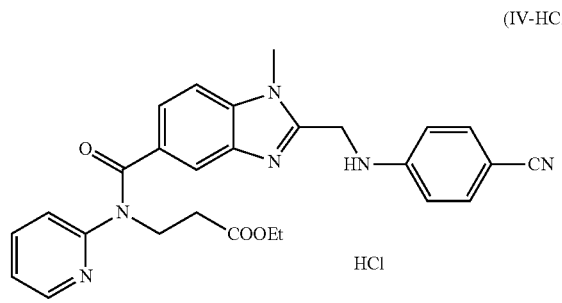

with hydrochloric acid and ethanol, and isolating the product obtained as a solid.

15. A process of preparing the compound of formula (IV-HCl) as defined in claim 3, in solid form comprising
(i) reacting the compound of formula (VI)

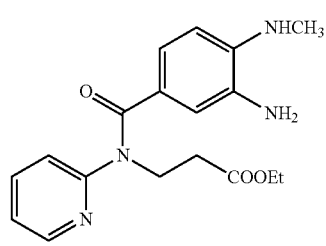

with the compound of formula (V)

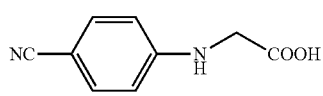

in the presence of a coupling agent, and subsequent cyclization with a cyclization agent to yield the compound of formula (IV); and
(ii) reacting the product obtained with hydrochloric acid to yield the compound of formula (IV-HCl), and isolating the product obtained as a solid.

16. The process according to claim 2, wherein the compound of formula (IV)

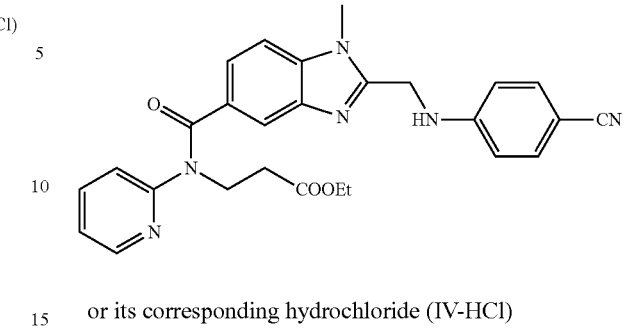

or its corresponding hydrochloride (IV-HCl)

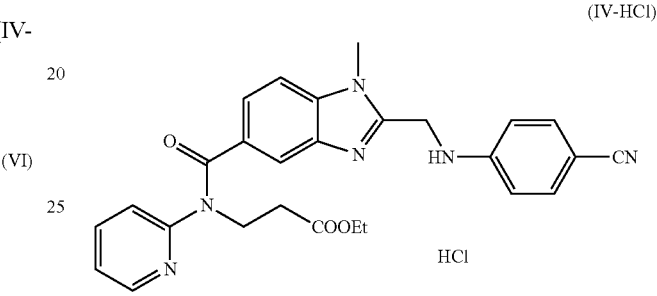

is previously reacted with hydrochloric acid and ethanol, optionally in the presence of a cosolvent, to yield the compound of formula (III-HCl), and isolating the product obtained as a solid.

17. The process according to claim 16, wherein the starting compound is the compound of formula (IV-HCl).

18. The process according to claim 17, wherein the cosolvent is toluene.

19. A process of preparing the crystalline form of the compound of formula (II-HCl) as defined in claim 10, by providing a compound of formula (II-HCl), recrystallizing it from isopropanol, and drying the solid obtained at about 65° C. under vacuum.

20. The process according to claim 19, wherein a compound of formula (III-HCl) in solid form is previously reacted with an amount comprised between 3-5 mol of ammonia or of an ammonium salt for each mol of the compound of formula (III-HCl) to obtain the compound of formula (II-HCl).

* * * * *